US009283296B2

(12) United States Patent
Haran et al.

(10) Patent No.: US 9,283,296 B2
(45) Date of Patent: Mar. 15, 2016

(54) SCENT PRODUCING APPARATUS

(75) Inventors: Yossi Haran, Modi'in-Macabim-Reut (IL); Tsafrir Sasson, Kibutz Maagan Michael (IL); Joseph Slupsky, Ramat Hasharon (IL)

(73) Assignee: SCENTCOM, LTD., Kibbutz Lehavot Haviva ( * ) Notice: Subject to any disclaimer, the term of this patent is extended or adjusted under 35 U.S.C. 154(b) by 245 days.

(21) Appl. No.: 13/981,772

(22) PCT Filed: Jan. 26, 2012

(86) PCT No.: PCT/IL2012/050025
§ 371 (c)(1),
(2), (4) Date: Aug. 28, 2013

(87) PCT Pub. No.: WO2012/101642
PCT Pub. Date: Aug. 2, 2012

(65) Prior Publication Data
US 2013/0334336 A1    Dec. 19, 2013

Related U.S. Application Data

(63) Continuation-in-part of application No. 13/143,202, filed as application No. PCT/IL2010/000016 on Jan. 7, 2010, now Pat. No. 8,727,234.

(60) Provisional application No. 61/143,283, filed on Jan. 8, 2009, provisional application No. 61/436,197, filed on Jan. 26, 2011.

(51) Int. Cl.
*B05B 17/06*    (2006.01)
*A61L 9/14*    (2006.01)
*B05B 17/00*    (2006.01)

(52) U.S. Cl.
CPC ............. *A61L 9/14* (2013.01); *B05B 17/0646* (2013.01); *B05B 17/0684* (2013.01); *A61L 2209/11* (2013.01); *A61L 2209/132* (2013.01); *A61L 2209/133* (2013.01)

(58) Field of Classification Search
CPC ......... A61L 9/14; A61L 9/04; A61L 2209/11; A61L 2209/132; A61L 2209/133; B05B 5/00; B05B 17/0646; B05B 17/0684
USPC ............. 239/4, 34, 52, 57, 102.1, 102.2, 302, 239/303, 304, 305
See application file for complete search history.

(56) References Cited

U.S. PATENT DOCUMENTS 4,695,434 A    9/1987   Spector
4,850,534 A    7/1989   Takahashi et al.
(Continued)

FOREIGN PATENT DOCUMENTS

EP    1329228 A1    7/2003
EP    1543844 A2    6/2005
(Continued)

OTHER PUBLICATIONS

International Search Report for PCT/IL2012/050025 mailed Sep. 7, 2012 by European Patent Office.
(Continued)

*Primary Examiner* — Justin Jonaitis
(74) *Attorney, Agent, or Firm* — PYI Tech, Ltd.; Simon Kahn; Chanoch Kahn

(57) ABSTRACT

A scent producing apparatus constituted of: a control circuitry; a plate exhibiting at least one release port extending from a first face of the plate to a second face of the plate opposing the first face; at least one scent reservoir in communication with the first face of the plate; a controllable scent release mechanism associated with each scent reservoir and arranged to release a controlled quantity of the contents of the associated scent reservoir through a release port to the second face of the plate; and a vibrator responsive to the control circuitry and in communication with the plate, wherein the control circuitry is arranged to: control each controllable scent release mechanism to release a controlled quantity of the contents of the associated scent reservoir through the release port to the second face of the plate; and vibrate the plate to thereby atomize the released contents.

25 Claims, 15 Drawing Sheets

(56) References Cited

U.S. PATENT DOCUMENTS

| | | | |
|---|---|---|---|
| 5,435,282 A | 7/1995 | Haber et al. | |
| 5,972,290 A | 10/1999 | De Sousa | |
| 6,024,783 A | 2/2000 | Budman | |
| 6,136,277 A | 10/2000 | Nardini | |
| 6,149,873 A | 11/2000 | Potter et al. | |
| 6,152,829 A | 11/2000 | Jaidka | |
| 6,325,475 B1 | 12/2001 | Hayes et al. | |
| 6,530,370 B1 | 3/2003 | Heinonen | |
| 6,536,746 B2 | 3/2003 | Watkins | |
| 6,539,937 B1 | 4/2003 | Haveri | |
| 6,581,915 B2 | 6/2003 | Bartsch et al. | |
| 6,592,104 B2 | 7/2003 | Cox | |
| 6,602,475 B1 | 8/2003 | Chiao | |
| 6,656,041 B1 | 12/2003 | Kaminkow | |
| 6,962,151 B1 | 11/2005 | Knoch et al. | |
| 7,040,548 B2 | 5/2006 | Rodgers | |
| 7,160,515 B2 | 1/2007 | Murdell et al. | |
| 7,223,361 B2 | 5/2007 | Kvietok et al. | |
| 7,437,061 B2 | 10/2008 | Manne | |
| 8,469,293 B2 * | 6/2013 | Doty et al. | 239/448 |
| 2003/0107139 A1 | 6/2003 | Wohrle | |
| 2003/0206834 A1 | 11/2003 | Chiao et al. | |
| 2004/0164101 A1 | 8/2004 | Cornet et al. | |
| 2006/0011739 A1 * | 1/2006 | Jaworski | A01M 1/205 239/102.2 |
| 2006/0289673 A1 | 12/2006 | Wang et al. | |
| 2007/0189919 A1 | 8/2007 | Prince et al. | |
| 2007/0258849 A1 | 11/2007 | Kent | |
| 2008/0043204 A1 | 2/2008 | Guo | |
| 2008/0191370 A1 | 8/2008 | Pankhurst et al. | |
| 2011/0266359 A1 * | 11/2011 | Haran | 239/6 |

FOREIGN PATENT DOCUMENTS

| | | |
|---|---|---|
| WO | 0012143 | 3/2000 |
| WO | 00/53301 A1 | 9/2000 |
| WO | 0232470 A1 | 4/2002 |
| WO | 03028775 A1 | 4/2003 |
| WO | 03059403 A1 | 7/2003 |
| WO | 2004/043502 A1 | 5/2004 |
| WO | 2004105878 A1 | 12/2004 |
| WO | 2005092400 A1 | 10/2005 |
| WO | 2006058125 A2 | 6/2006 |
| WO | 2006074562 A1 | 7/2006 |
| WO | 2010079485 A1 | 7/2010 |

OTHER PUBLICATIONS

Written Opinion of the International Searching Authority for PCT/IL2012/050025 mailed Sep. 7, 2012 by European Patent Office.

* cited by examiner

SCENT PRODUCING APPARATUS

CROSS-REFERENCE TO RELATED APPLICATIONS

This application is a National Phase application of PCT/IL2012/050025 with International Filing Date Jan. 26, 2012, and which PCT/IL2012/050025 claims priority from U.S. Provisional Application 61/436,197 filed Jan. 26, 2011. Additionally, this application is a continuation-in-part of U.S. patent application Ser. No. 13/143,202 which is a National Phase application of PCT/IL2010/000016 with International Filing Date Jan. 7, 2010, and which PCT/IL2010/000016 claims priority from U.S. Provisional Application 61/143,283 filed Jan. 8, 2009.

TECHNICAL FIELD

The invention relates generally to the field of electronically controlled scent production, and more particularly to an apparatus with an electronically controlled atomizer arranged to produce a scent on a first face of the atomizer responsive to scent liquid stored in a scent reservoir in communication with a second, opposing face of the atomizer.

BACKGROUND

Video games, particularly computer based games and game stations, have become extremely popular. The combination of visual and audio stimulation has succeeded in capturing a significant portion of people's leisure time. Various games have been developed, with associated hardware, that further involves the sense of touch, by allowing for varying input instruments. In one example, a musical instrument such as a mock guitar, is utilized as a game input, thus involving the sense of touch.

Games have been developed providing for a virtual reality world, again based on stimulating various user senses. However, to date, the remaining senses, namely smell and taste have not been stimulated.

While the above has been described in relation to games, this is not meant to be limiting in any way. Many other uses of an electronically controlled scent system exist, such as alarms, the improvement of communication, and mood enhancements, without limitation, are specifically included herein.

U.S. Patent Application Publication S/N 2008/0043204 published Feb. 21, 2008 to Guo, is addressed to a digital scent movie projector with sound channels. Scent making devices release a scent into a cinema, thereby providing for film arts to provide a sense of sight, hearing and smell as part of movie. Unfortunately, scent provided by Guo is arranged to be released into a large space, which is not appropriate for an individual use. Furthermore, the scent of Guo utilizes a plurality of scent cans feeding pressure reducing valves, and is thus limited in terms of its ability to accurately control the amount of persistence of the scent.

Various nebulizer schemes are known to the prior art, including placing a vibrating fine mesh in contact with a liquid to be nebulized. The mesh typically is arranged to be sufficiently fine so as to block any flow of the liquid and is vibrated, typically at ultrasonic frequencies, thereby atomizing the liquid. Unfortunately, such a scheme suffers from certain drawbacks, such as spontaneous scent leakage since there is no means to prevent spontaneous release of volatile vapors via the mesh opening. Furthermore, any molecules adhering to the mesh walls may be released without further vibration, further leading to undesired scent persistence. Additionally, there is a tendency for the fine mesh to become blocked by organic and/or inorganic molecules, such as aqueous salts adhering to the mesh openings. Furthermore, micro-droplets cannot be properly formed from liquid with a viscosity of greater than 10 cps and thus the liquid will not be atomized sufficiently. Furthermore, the mesh aperture which is fixed in size is designed for producing a desired droplet size for a viscosity and surface tension of a particular liquid, and a particular fixed mesh based nebulizer can not be used for any of a plurality of liquids having a range of viscosity without changing the fixed mesh. Additionally, vibrating the mesh at frequencies of greater than 1 Mhz, which is preferred for improved atomization, will cause less effective atomization because of the properties of the mesh.

U.S. Pat. No. 4,301,093 issued on Nov. 17, 1981 to Eck, the entire contents of which are incorporated herein by reference, is addressed to a liquid atomizer where liquid is disposed on a face of an atomizer plate, where it is then atomized. Disadvantageously, the disposed liquid is open to the ambient air, which raises persistence issues.

U.S. Patent Application Publication S/N 2011/0266359 published Nov. 3, 2011 to Haran, the entire contents of which is incorporated herein by reference, is addressed to an electronically controlled scent producing element comprising an atomizer constituted of a first plate exhibiting a plurality of micro-plugs and a second plate exhibiting a plurality of perforations, the micro-plugs arranged to mate with the perforations. Scent liquid is then atomized by the atomizer. Disadvantageously, vibrating the disclosed atomizer at frequencies greater than 1 Mhz, which is preferred for improved atomization, will cause less effective atomization because of the properties of the atomizer. Additionally, micro-droplets cannot be properly formed from liquid with a viscosity of greater than 10 cps and thus the liquid will not be atomized sufficiently.

Additionally, many prior art solutions suffer from residual scent, i.e. undesired scent persistence. Residual scent is particularly problematic in the case of individual scent needs, such as computer gamers, which often play in undisturbed spaces, where scents easily linger. In particular, any physical element which has been contacted by a concentration of scent molecules continues to exude the scent. The residual scent further contaminates additional scents, which may need to be rapidly emitted in line with progress of the game.

SUMMARY

Accordingly, it is a principal object of the present invention to overcome at least some of the disadvantages of prior art. This is accomplished in certain embodiments by providing a scent producing apparatus, the apparatus comprising: a control circuitry; a plate exhibiting at least one release port extending from a first face of the plate to a second face of the plate opposing the first face; at least one scent reservoir in communication with the first face of the plate; a controllable scent release mechanism associated with each scent reservoir and arranged to release a controlled quantity of the contents of the associated scent reservoir through the at least one release port to the second face of the plate; and a vibrator responsive to the control circuitry and in communication with the plate, wherein the control circuitry is arranged to: control each controllable scent release mechanism to release a controlled quantity of the contents of the associated scent reservoir through the at least one release port to the second face of the plate; and vibrate the plate to thereby atomize the released contents of the at least one scent reservoir.}

In one embodiment, each controllable scent release mechanism comprises a local portion of the at least one scent reservoir. In another embodiment, each controllable scent release mechanism further comprises: a scent release micro-needle, in communication with the first face of the plate, extending longitudinally from a base end to a tip end, and arranged to mate with a respective release port; and a scent release translation mechanism in communication with the scent release micro-needle and responsive to the control circuitry, wherein the control circuitry is further arranged to translate, via the scent release translation mechanism, the scent release micro-needle in relation to the plate from a first position, wherein the scent release micro-needle is seated within the respective release port, to a second position wherein the scent release micro-needle is at least partially removed from a wall of the respective release port, and wherein the control of each controllable release mechanism to release a controlled quantity of the contents of the associated scent reservoir is responsive to the respective scent release micro-needle being in the second position. In one further embodiment, the scent release translation mechanism comprises a scent release piezoelectric element.

In one embodiment, the controllable scent release mechanism comprises a scent release piezoelectric element. In another embodiment, the at least one scent reservoir comprises a plurality of scent reservoirs and the at least one release port comprises a plurality of release ports each associated with a particular controllable scent release mechanisms, the arrangement of the control circuitry to control each controllable scent release mechanism to release a controlled quantity of the contents of the associated scent reservoir comprises an arrangement to control each controllable scent release mechanism to release a controlled quantity of the contents of the associated scent reservoir through the associated release port to the second face of the plate.

In one embodiment, the scent producing apparatus further comprises: a solvent reservoir in communication with the first face of the plate; and at least one controllable solvent release mechanism associated with the solvent reservoir and arranged to release a controlled quantity of the contents of the solvent reservoir through the at least one release port to the second face of the plate, wherein the control circuitry is further arranged to control the at least one controllable solvent release mechanism to release a controlled quantity of the contents of the solvent reservoir through the at least one release port to the second face of the plate. In one further embodiment, each controllable solvent release mechanism further comprises a local portion of the solvent reservoir.

In another further embodiment, each controllable solvent release mechanism further comprises: a solvent release micro-needle, in communication with the first face of the plate, extending longitudinally from a base end to a tip end, and arranged to mate with a respective release port; and a solvent release translation mechanism in communication with the solvent release micro-needle and responsive to the control circuitry, wherein the control circuitry is further arranged to translate, via the solvent release translation mechanism, the solvent release micro-needle in relation to the plate from a first position, wherein the solvent release micro-needle is seated within the respective release port, to a second position wherein the solvent release micro-needle is at least partially removed from a wall of the respective release port, and wherein the control of each controllable release mechanism to release a controlled quantity of the contents of the solvent reservoir is responsive to the respective solvent release micro-needle being in the second position. In one yet further embodiment, the solvent release translation mechanism comprises a solvent release piezoelectric element.

In one further embodiment, the controllable solvent release mechanism comprises a solvent release piezoelectric element. In another further embodiment, the at least one controllable scent release mechanism comprises a plurality of controllable scent release mechanisms, and wherein the at least one controllable solvent release mechanism comprises a plurality of controllable solvent release mechanisms, each associated with a particular one of the plurality of controllable scent release mechanisms. In one embodiment, each scent reservoir comprises a scented material.

In independent embodiment, a method of producing a scent is provided, the method comprising: providing a plate exhibiting at least one release port extending from a first face of the provided plate to a second face of the provided plate opposing the first face; providing at least one scent reservoir in communication with the first face of the provided plate; releasing a controlled quantity of the contents of the provided at least one scent reservoir through the at least one release port to the second face of the provided plate; and vibrating the provided plate to thereby atomize the released contents of the provided at least one scent reservoir.

In one embodiment, the method further comprises: providing a controllable scent release mechanism associated with each provided scent reservoir, the releasing a controlled quantity of the contents of each provided scent reservoir being responsive to the provided associated controllable scent release mechanism, wherein each provided controllable scent release mechanism comprises a local portion of the provided associated scent reservoir. In one further embodiment, each provided controllable scent release mechanism further comprises: a scent release micro-needle, in communication with the first face of the provided plate, extending longitudinally from a base end to a tip end, and arranged to mate with a respective release port, wherein the method further comprises translating the scent release micro-needle in relation to the provided plate from a first position, wherein the scent release micro-needle is seated within the respective release port, to a second position wherein the scent release micro-needle is at least partially removed from a wall of the respective release port, and wherein the releasing a controlled quantity of the contents of the provided at least one scent reservoir is responsive to the respective scent release micro-needle being in the second position.

In one yet further embodiment, the method further comprises: providing a scent release piezoelectric element in communication with the local portion of each provided scent reservoir, wherein the translating each scent release micro-needle comprises applying an electrical signal to the associated provided scent release piezoelectric element. In another embodiment, the method further comprises: providing a scent release piezoelectric element in communication with each provided scent reservoir, wherein the releasing a controlled quantity of the contents of each provided scent reservoir comprises applying an electrical signal to the associated provided scent release piezoelectric element.

In one embodiment, the provided at least one scent reservoir comprises a plurality of scent reservoirs and the at least one release port comprises a plurality of release ports each associated with a particular scent reservoir, the releasing a controlled quantity of the contents of each provided scent reservoir comprises releasing a controlled quantity of the contents of the particular provided scent reservoir through the associated release port to the second face of the provided plate. In another embodiment, the method further comprises: providing a solvent reservoir in communication with the first face of the plate; and releasing a controlled quantity of the contents of the provided solvent reservoir through the at least one release port to the second face of the provided plate.

In one yet further embodiment, the method further comprises: providing at least one controllable solvent release mechanism associated with the provided solvent reservoir, the releasing a controlled quantity of the contents of the provided solvent reservoir being responsive to the provided at least one controllable solvent release mechanism, wherein each controllable solvent release mechanism further comprises a local portion of the provided solvent reservoir. In one yet even further embodiment, each provided controllable solvent release mechanism further comprises: a solvent release micro-needle, in communication with the first face of the provided plate, extending longitudinally from a base end to a tip end, and arranged to mate with the at least one release port, wherein the method further comprises translating the solvent release micro-needle in relation to the provided plate from a first position, wherein the solvent release micro-needle is seated within the respective release port, to a second position wherein the solvent release micro-needle is at least partially removed from a wall of the respective release port, and wherein the releasing a controlled quantity of the contents of the provided solvent reservoir is responsive to at least one scent release micro-needle being in the second position.

In one yet additional further embodiment the method further comprises: providing a solvent release piezoelectric element in communication with each local portion of the provided solvent reservoir, wherein the translating each solvent release micro-needle comprises applying an electrical signal to the associated provided solvent release piezoelectric element. In another yet further embodiment, the method further comprises: providing a solvent release piezoelectric element in communication with each local portion of the provided solvent reservoir, wherein the releasing a controlled quantity of the contents of the provided solvent reservoir comprises applying an electrical signal to a provided solvent release piezoelectric element.

In one yet further embodiment, the at least one controllable scent release mechanism comprises a plurality of controllable scent release mechanisms, and wherein the at least one controllable solvent release mechanism comprises a plurality of controllable solvent release mechanisms, each associated with a particular one of the plurality of controllable scent release mechanisms In one embodiment, each provided scent reservoir comprises a scented material. In another embodiment, the method further comprises: releasing a pre-determined quantity of neutralizing agent through the at least one release port onto the second face of the provided plate, wherein the vibrating atomizes the released contents of the provided at least one scent reservoir and the released neutralizing agent.

Additional features and advantages of the invention will become apparent from the following drawings and description.

BRIEF DESCRIPTION OF THE DRAWINGS

For a better understanding of various embodiments of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION

Figure 1A:
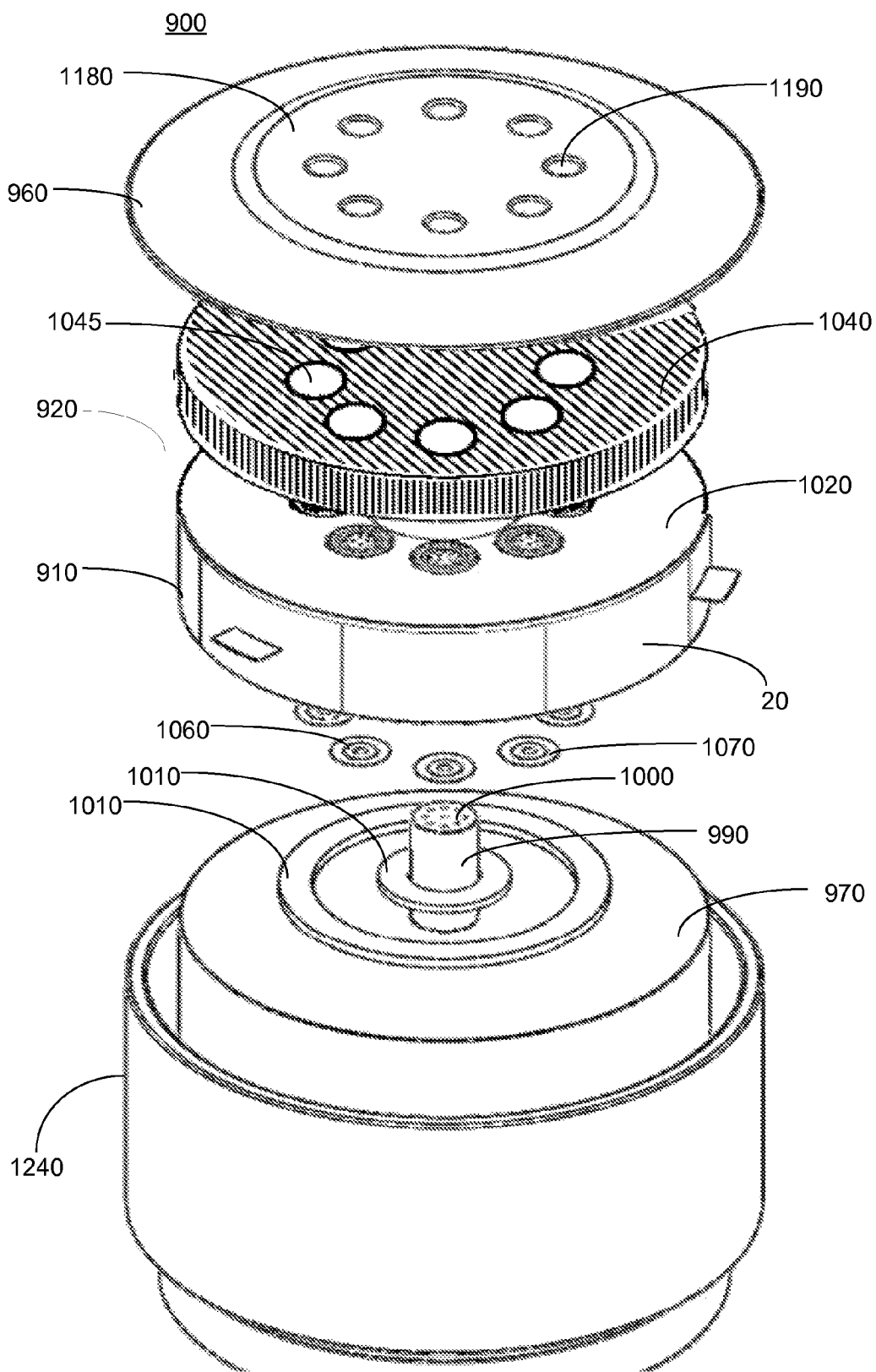
FIGS. 1A-1I illustrate a plurality of views of an exemplary embodiment of a scent producing apparatus comprising a multi-scent cartridge in communication with an atomizer.

Before explaining at least one embodiment in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

The term atomizer, as used herein, is meant to include any apparatus arranged to nearly instantly convert a liquid into a fine mist, and is synonymous with the term nebulizer, with the difference that the term nebulizer it typically used to indicate that the apparatus is slow to atomize, and exhibits less control over the amount of fine mist created responsive to a command.

Figure 1B:
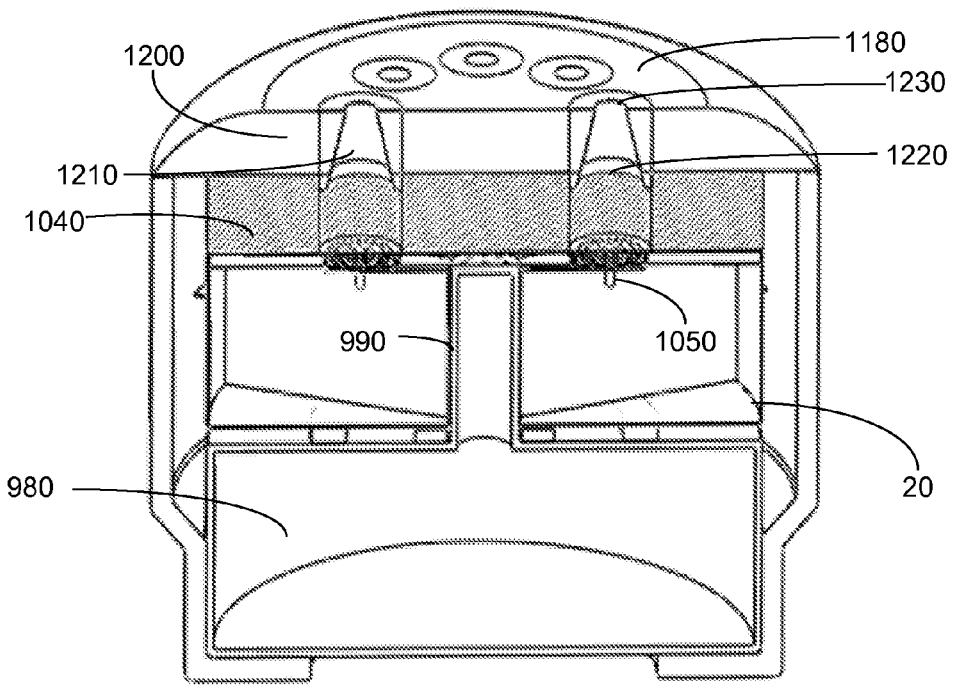
Figure 1C:
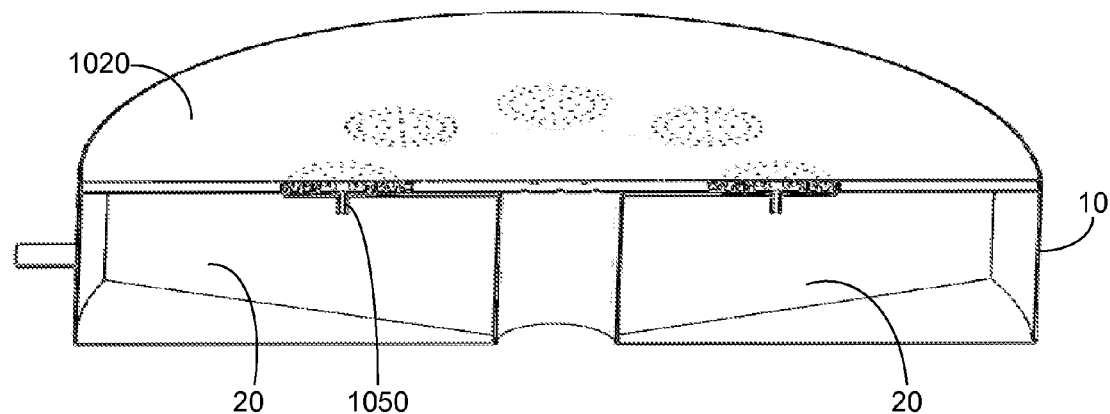
Figure 1D:
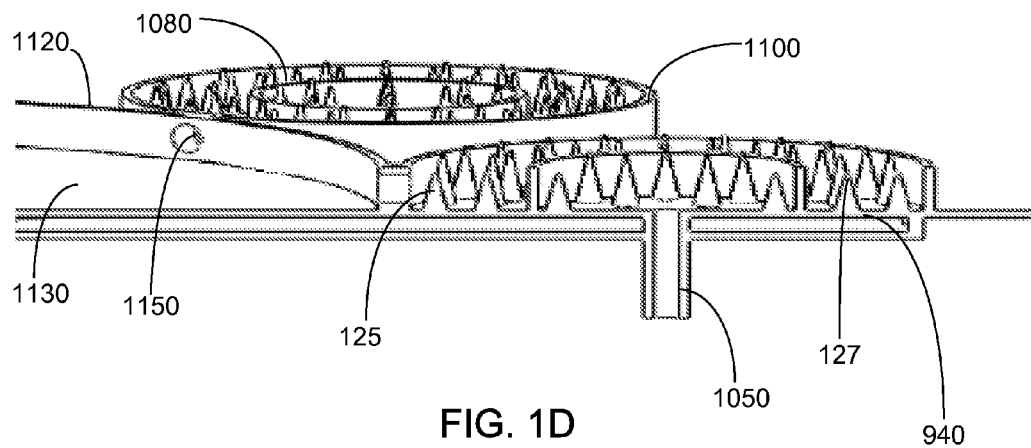
Figure 1E:
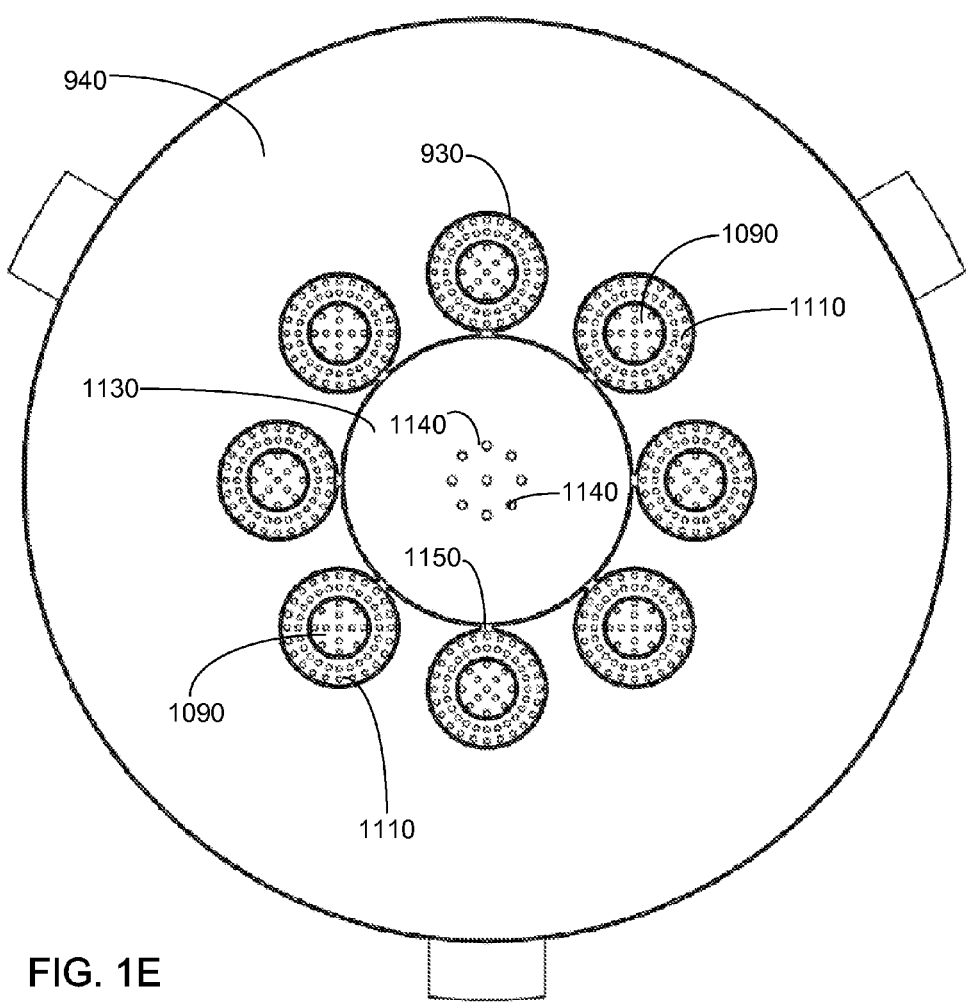
Figure 1F:
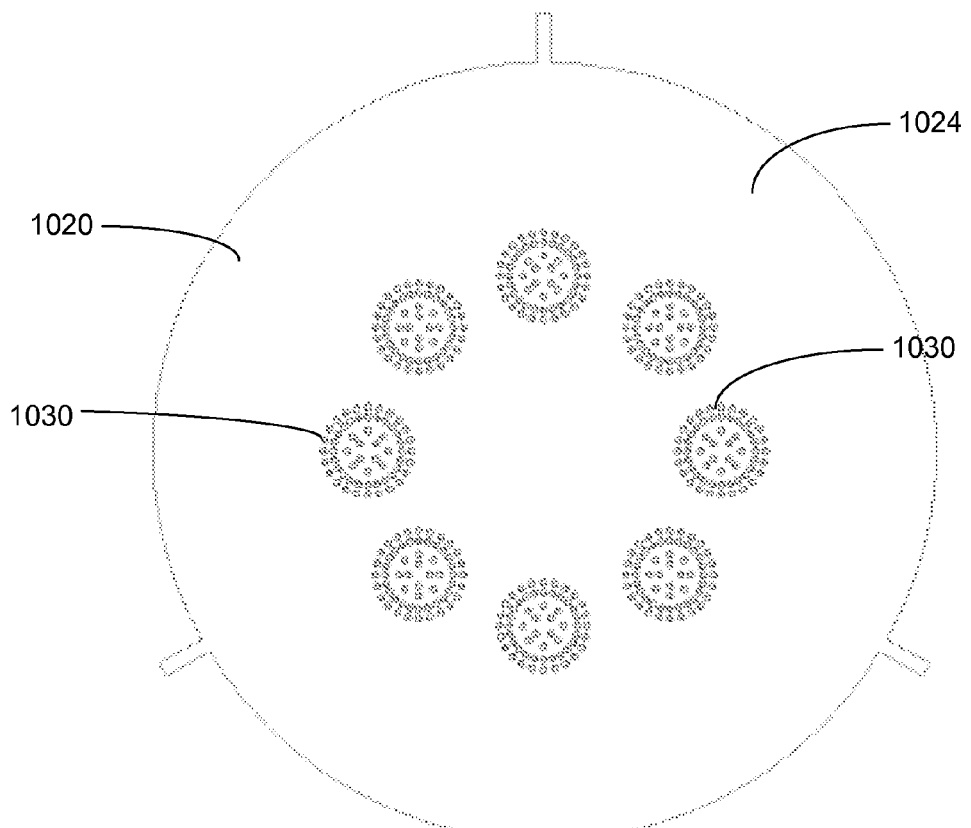
Figure 1G:
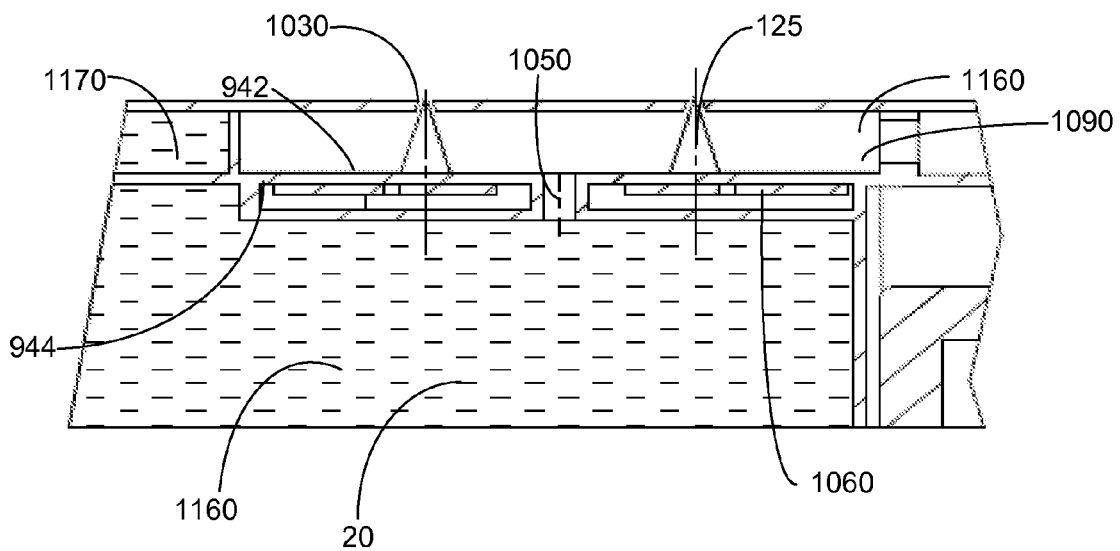
Figure 1H:
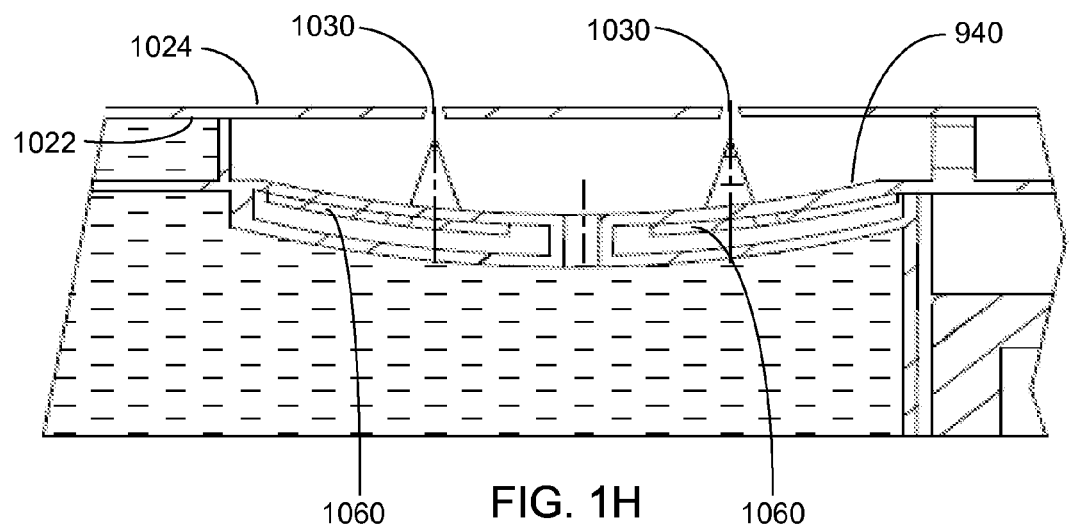
Figure 1I:
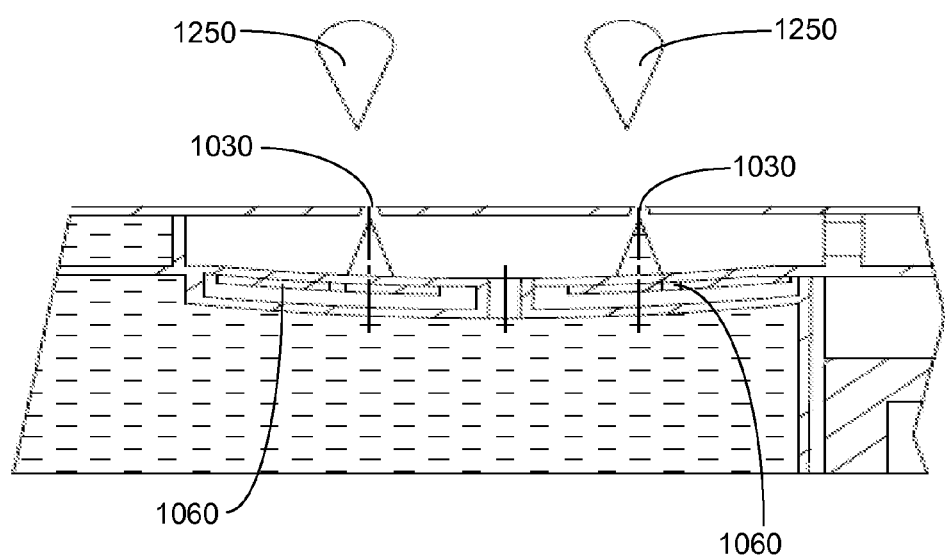
Figure 2:
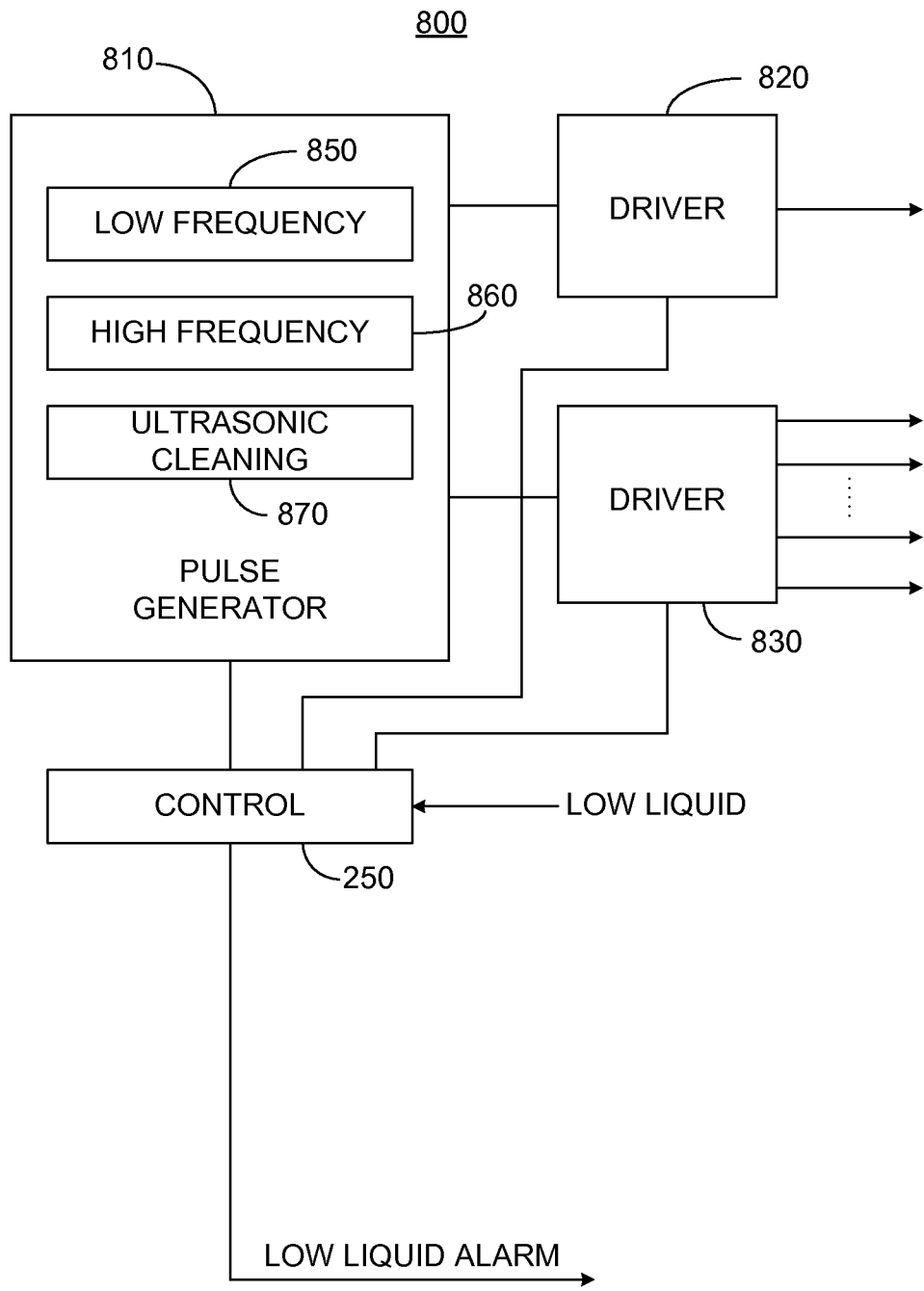
FIG. 2 illustrates a high level schematic diagram of a driving circuitry for controllably driving the scent producing apparatus of FIGS. 1A-1I.

FIG. 1A illustrates a perspective view of various components of a scent producing apparatus 900, comprising a multi-scent cartridge 910 in communication with an atomizer 920; FIG. 1B illustrates a side cut view of scent producing apparatus 900; FIG. 1C illustrates a side cut view of multi-scent cartridge 910 in communication with atomizer 920 and exhibiting a plurality of controllable release mechanisms 930; FIG. 1D illustrates a side cut view of plurality of controllable release mechanisms 930 disposed on a common base 940, each controllable release mechanism 930 comprising a plurality of optional micro-needles 125; FIG. 1E illustrates a top view of the plurality of controllable release mechanisms 930 disposed on common base 940; FIG. 1F illustrates a top view of an atomizer plate 1020; FIG. 1G illustrates a side cut view of a controllable release mechanism 930 with optional micro-needles 125 in a first position; FIG. 1H illustrates a side cut view of a controllable release mechanism 930 with optional micro-needles 125 in a second position; and FIG. 1I illustrates a side cut view of a controllable release mechanism 930 with optional micro-needles 125 in a third position, FIGS. 1A-1I being taken together.

In further detail, scent producing apparatus 900 comprises: multi-scent cartridge 910; atomizer 920; plurality of controllable release mechanisms 930; common base 940, exhibiting a first face 942 and a second face 944 opposing first face 942; a segmented nozzle device 960; a housing 970, forming a solvent reservoir 980; a housing extension 990, exhibiting a plurality of solvent exit ports 1000; and a pair of vibration isolation rings 1010. Atomizer 920 comprises: an atomizer plate 1020, exhibiting a first face 1022, a second face 1024 opposing first face 1022 and a plurality of release ports 1030 extending from first face 1022 to second face 1024, each release port 1030 forming the chassis section of a particular micro-valve; and a vibration mechanism 1040. In one embodiment, release ports 1030 are separated from each other by at least 300 microns. In one embodiment, vibration mechanism 1040 comprises a piezoelectric element. In one embodiment, vibration mechanism 1040 is disc shaped and exhibits a plurality of holes 1045 extending therethrough, each hole 1045 arranged to be aligned with the plurality of micro-valves associated with a particular controllable release mechanism 930. In another embodiment (not shown), vibration mechanism 1040 is ring shaped.

Each controllable release mechanism 930 comprises: a plurality of optional micro-needles 125 extending longitudinally from common base 940 to a tip end 127, each optional micro-needle 125 forming the needle section of a particular micro-valve, as will be described below; an input port 1050; a first translation mechanism 1060; a second translation mechanism 1070; a local scent reservoir border ring 1080, extending from common base 940 to atomizer plate 1020 and forming a local portion 1090 of the respective scent reservoir 20, as will be described further below; and a local solvent reservoir border ring 1100 extending from common base 940 to atomizer plate 1020 and forming with local scent reservoir border ring 1080 a local portion 1110 of solvent reservoir 980, as will be described further below. In one embodiment, the distance between common base 940 and atomizer plate 1020 is 100-300 microns. In one embodiment, first and second translation mechanisms 1060, 1070 are provided as a single translation mechanism, implemented in one particular embodiment as a piezo-electric element, without exceeding the scope. In one embodiment (not illustrated), each of the first and second translation mechanisms 1060, 1070 comprises an electrode arranged to provide an electric power to the respective translation mechanism 1060, 1070, the electrode receiving power from a control circuitry. In one embodiment the diameter of each optional micro-needle 125 at common base 940 is 25-50 microns and in one further embodiment is about 30 microns.

Segmented nozzle device 960 comprises: a surface 1180, exhibiting a plurality of apertures 1190; and a nozzle extension 1200 comprising a plurality of nozzles 1210, each exhibiting an entry port 1220 and an exit port 1230, with each exit port 1230 constituted of a particular aperture 1190.

Common base 940 has disposed on first face 942 a plurality of controllable release mechanism 930, preferably radially displaced from each other. Common base 940 has further disposed on first face 942 a temporary solvent reservoir border ring 1120, extending from common base 940 to atomizer plate 1020 and forming a temporary solvent reservoir 1130 exhibiting a plurality of solvent entry ports 1140 extending through common base 940. Temporary solvent reservoir border ring 1120 exhibits a plurality of solvent passes 1150 therethrough, each arranged to provide communication between temporary solvent reservoir 1130 and each local portion 1110 of solvent reservoir 980 through the respective local solvent reservoir border ring 1100. In particular, at least one solvent pass 1150 is provided for each local portion 1110 of solvent reservoir 980. Each first translation mechanism 1060 is in communication with the respective local portion 1090 of scent reservoir 20 and particularly in communication with the area of second face 944 of common base 940 opposing the respective local portion 1090 of scent reservoir 20. Each second translation mechanism 1070 is in communication with the respective local portion 1110 of solvent reservoir 980 and particularly in communication with the area of second face 944 of common base 940 opposing the respective local portion 1110 of solvent reservoir 980.

Each of the plurality of optional micro-needles 125 is arranged to mate with a respective one of release ports 1030, thereby forming a micro-valve, the plurality of micro-valves forming a micro-valve array. Preferably, a portion of each optional micro-needle 125, and particularly the portion extending through release ports 1030 are conically shaped with an apex extending away from common base 940. Release ports 1030 are preferably similarly conically shaped, such that when the respective optional micro-needles 125 are in the first position, as will be described below, each of the respective optional micro-needles 125 is seated against the inner walls of the respective release port 1030, thus forming a seal sufficient to prevent the flow of volatile scent liquid 1160 through the respective release port 1030. In one embodiment, optional micro-needles 125 are seated flush again the inner walls of the respective release port 1103 thus forming a seal. Preferably, each release port 1030 exhibits a diameter of about 30 optional microns at first face 1022 of atomizer plate 1020, matching the diameter of optional micro-needles 125 when completely seated therein.

Each scent reservoir 20 comprises volatile scent liquid 1160. Preferably, volatile scent liquid 1160 is super-concentrated. Each controllable release mechanism 930 is associated with one of the plurality of scent reservoirs 20 and each input port 1050 extends through common base 940 into the respective scent reservoir 20. Preferably, each input port 1050 comprises a one-way valve, allowing for volatile scent liquid 1160 to flow only into the respective local portion 1090 of the respective scent reservoir 20.

Solvent reservoir 980 comprises common solvent 1170. The term common solvent is used herein as a solvent used for the contents of each of the scent reservoirs 20, and in one particular embodiment is water. Housing extension 990 extends through multi-scent cartridge 910 and is in communication with common base 940, with each of the plurality of solvent exit ports 1000 in communication with a respective one of the plurality of solvent entry ports 1140 and forming a pass for common solvent 1170 into temporary solvent reservoir 1130. Preferably, housing extension 990 comprises a one-way valve, allowing for common solvent 1170 to flow only into local solvent reservoir 1130. Vibration mechanism 1040 is in communication with second face 1024 of atomizer plate 1020. Vibration isolation rings 1010 are arranged to isolate housing 970 from multi-scent cartridge 910 such that when multi-scent cartridge 910 is vibrated, as will be described below, housing 970 is not vibrated. Entry port 1220 of each nozzle 1210 is in communication with second face 1024 of atomizer plate 1020 via a respective hole 1045 of vibration mechanism 1040. Specifically, entry port 1220 of each nozzle 1210 is in communication with the plurality of micro-valves associated with a particular controllable release mechanism 930. In one embodiment, housing 970, multi-scent cartridge 910, atomizer 920 and nozzle extension 1200 are placed inside an outer housing 1240.

In one embodiment, housing 970 is removable and solvent reservoir 980 can be refilled when exhausted of common solvent 1170. In another embodiment, an opening (not shown) is provided in housing 970 to allow refilling of solvent reservoir 980 when exhausted of common solvent 1170. In one embodiment, multi-scent cartridge 910 is removable from scent producing apparatus 900 and can be replaced with a new multi-scent cartridge 910 when one or more scent reservoirs 20 are exhausted of volatile scent liquid 1160. In another embodiment, openings are provided to the plurality of scent reservoirs 20 (not shown) to allow refilling of any of the plurality of scent reservoirs 20 when exhausted of volatile scent liquid 1160.

Common solvent 1170 stored in solvent reservoir 980 is arranged to enter housing extension 990, aided by the force of gravity. In an alternative embodiment (not shown) a positive pressure mechanism is supplied. Common solvent then 1170 enters temporary solvent reservoir 1130 and via solvent passes 1150 to each local portion 1110 of solvent reservoir 980. Volatile scent liquid 1160 from each scent reservoir 20 enters the respective local portion 1090 via the respective input port 1050. In one embodiment, the volatile scent liquid 1160 flows through input port 1050 aided by the force of gravity, as described above in relation to common solvent 1170. In another embodiment, volatile scent liquid 1160 flows through input port 1050 aided by capillary action.

In an embodiment where optional micro-needles 125 are not provided, the diameter of release ports 1030 are arranged to be small enough such that volatile scent liquid 1160 and common solvent 1170 stored in a controllable release mechanism 930 cannot exit through the respective release ports 1030 solely in response to gravity, the diameter of release ports 1030 being selected responsive to the viscosity of the volatile scent liquid 1160 and common solvent 1170.

In operation, each controllable release mechanism 930 is arranged to release a controlled amount of volatile scent liquid 1160 from a particular associated scent reservoir 20, and common solvent 1170 into atomizer 920, as described further below. In a first position, wherein first translation mechanism 1060 and second translation mechanism 1070 are each not contracted, in one embodiment each optional micro-needle 125 is seated against the walls of the respective release port 1030, thereby closing the respective release port 1030. In one embodiment, optional micro-needles 125 are seated flush again the inner walls of the respective release port 1103 thus forming a seal closing the respective release port 1030. In order to release a controlled quantity of volatile scent liquid 1160 and common solvent 1170 from a particular controllable release mechanism 930, a low frequency electrical signal and a DC electrical signal are provided by control circuitry 250 of FIG. 4 (not shown) to the associated first translation mechanism 1060 and second translation mechanism 1070. At a high state of the low frequency signal, first and second translation mechanisms 1060 and 1070 are contracted, thereby bending common base 940 and translating optional micro-needles 125 to a second position, wherein optional micro-needles 125 are removed from release ports 1030. In one embodiment, optional micro-needles 125, in the second position, are only partially removed from release ports 1030 so as to allow entry of volatile scent liquid 1160 or common solvent 1170 into the respective release ports 1030.

At a low state of the low frequency signal, first and second translation mechanisms 1060 and 1070 partially expand to translate optional micro-needles 125 to a third position, the third position being between the first position and the second position. First and second translation mechanisms 1060 and 1070 remain partially contracted because of the DC electrical signal. As optional micro-needles 125 are translated from the second position to the third position, droplets 1250 of volatile scent liquid 1160 and common solvent 1170 are released through the respective release port 1030 onto second face 1024 of atomizer plate 1020. Thus, droplets 1250 of volatile scent liquid 1160 and common solvent 1170 are released using Drop on Demand technology with the addition of optional micro-needles 125. Advantageously, in the first position optional micro-needles prevent volatile scent liquid 1160 and common solvent 1170 from being uncontrollably released through release ports 1030. Further advantageously, volatile scent liquid 1160 and common solvent 1170 are disposed onto second face 1024 of atomizer plate 1020 while being stored in communication with first face 1022 of atomizer plate 1020.

In the embodiment where optional micro-needles 125 are not provided, first and second translation mechanisms 1060 and 1070 are arranged to expand so as to release droplets 1250 of volatile scent liquid 1160 and common solvent 1170, as known to one skilled in the art of Drop on Demand technology. Specifically, when first and second translation mechanisms 1060 and 1070 expand, common base 940 bends thereby applying pressure to the volatile scent liquid 1160 and common solvent 1170. Responsive to the applied pressure, droplets 1250 of volatile scent liquid 1160 and common solvent 1170 are released through the respective release port 1030 onto second face 1024 of atomizer plate 1020.

Control circuitry 250 is further arranged to provide a high frequency electrical signal to vibration mechanism 1040 thereby vibrating atomizer plate 1020 and atomizing any droplets 1250 of volatile scent liquid 1160 and common solvent 1170 found on second face 1024 of atomizer plate 1020. In an exemplary embodiment the high frequency electrical signal exhibits a frequency range of 1-2 MHz, however this is not meant to be limiting in any way. The atomized droplets 1250 of volatile scent liquid 1160 and common solvent 1170 enter the associated nozzle 1210, via the entry port 1220, and travel through the nozzle 1210 and out through exit port 1230. The atomized droplets 1250 of volatile scent liquid 1160 and common solvent 1170 mix inside nozzle 1210, such that a scent is released external of segmented nozzle device 960. Advantageously, each of the various atomized droplets 1250 of volatile scent liquids 1160 in combination with common solvent 1170 meet externally of the respective exit port 1230, and are not mixed within scent producing apparatus 900. In particular, each of the scents from the respective scent reservoirs 20 are kept isolated from other scents by the operation of segmented nozzle device 960. Thus, production of a particular scent is not contaminated by other scents which may remain on the inner walls of segmented nozzle device 960.

Preferably, control circuitry 250 is arranged to provide the high frequency electrical signal to vibration mechanism 1040 during the release of droplets 1250 of volatile scent liquid 1160 and common solvent 1170. Advantageously, any liquid in the vicinity of release ports 1030 are atomized and do not interfere with the releasing of additional droplets 1250 of volatile scent liquid 1160 and common solvent 1170.

In one embodiment, the amount and size of optional micro-needles 125 in local portion 1090 of each scent reservoir 20 and each local portion 1110 of solvent reservoir 980 are chosen such that a predetermined quantity of common solvent 1170 is released for each released quantity of volatile scent liquid 1160. In one embodiment the quantity of released common solvent 1170 is about 20 times the quantity of released volatile scent liquid 1160. In one embodiment, the frequencies of the low frequency electrical signals provided to first translation mechanism 1060 and second translation mechanism 1070 are chosen such that a predetermined quantity of common solvent 1170 is released for each released quantity of volatile scent liquid 1160. In one embodiment, the high frequency electrical signal is provided to vibration mechanism 1040 at predetermined intervals and the lengths of time the low frequency electrical signals are provided to first translation mechanism 1060 and second translation mechanism 1070 are chosen such that a predetermined quantity of common solvent 1170 is released for each released quantity of volatile scent liquid 1160.

In order to cease the production of the scent, control circuitry 250 is arranged to disconnect electrical signals from vibration mechanism 1040, and in response atomizer plate 1020 ceases to vibrate. Control circuitry 250 is further arranged to disconnect electrical signal from the respective first and second translation mechanisms 1060 and 1070. In one embodiment, first and second translation mechanism 1060 and 1070 fully expand, thereby returning optional micro-needles 125 to the first position.

In order to produce a compound scent, control circuitry 250 applies a low frequency electric power to a plurality of first and second translation mechanisms 1060 and 1070, thereby releasing controlled quantities of different volatile scent liquids 1160 and common solvent 1170 through the respective release ports 1030, as described above. In one embodiment, each of the different volatile scent liquids 1160 produces a unique scent. A plurality of scents is then produced, as described above, each scent exiting a respective nozzle 1210. The plurality of scents mix as they exit the respective nozzles 1210, thereby creating a compound scent.

The above has been described in an embodiment wherein segmented nozzle device 960 is provided. Advantageously, each scent has a separate nozzle 1210 and therefore there is no requirement to clean atomizer plate 1020. In another embodiment, segmented nozzle device 960 is not provided, as illustrated below in relation to FIGS. 3A-3C. In such an embodiment, after the production of a scent is completed atomizer plate 1020 is ultrasonically cleaned. As described above, in one embodiment, at the end of scent production, optional micro-needles 125 are returned to the first position so that no droplets 1250 are released to second face 1024 of atomizer plate 1020. A medium to high frequency electrical signal, in one non-limiting embodiment being from 40 kHz to 400 kHz, is supplied to vibration mechanism 1040, thus vibrating atomizer plate 1020. Any residual volatile scent liquid 1160 and common solvent 1170 on second face 1024 of atomizer plate 1020 is promptly atomized, or nebulized, and removed completely, thus ceasing scent production, and cleaning the previously issued scent from second face 1024 of atomizer plate 1020, allowing for production of a different subsequent scent without any residual scent from the previous scent production. Advantageously, scent producing apparatus 900 can be used to produce a scent, ultrasonically cleaned and used again to produce a different scent.

In another embodiment, multi-scent cartridge 910 is provided with one or more neutralizer reservoirs in place of one or more scent reservoirs 20. Each neutralizer reservoir is provided with a neutralizing agent. In one embodiment the neutralizing agent is an amphoteric substance arranged to neutralize any scent produced by scent producing apparatus 900 after a pre-determined time period. In one particular embodiment the neutralizing agent is a sodium bicarbonate solution. In another embodiment the neutralizing agent is a strongly basic liquid, preferably exhibiting a pH of greater than 9 to neutralize any acidic volatile scent liquid. In one further embodiment, common solvent 1170 in reservoir 980 is replaced with a neutralizing agent. In one further embodiment, an additional reservoir comprising a neutralizing agent is provided and is arranged to release the neutralizing agent in parallel with, or alternately with, common solvent 1170. During production of a scent, droplets 1250 of neutralizing agent are released onto second face 1024 of atomizer plate 1020 in addition to, or in place of, the common solvent, as described above. Thus, scent is produced by atomizer 920 with a predetermined persistence. Advantageously, atomizer plate 1020 does not have to be ultrasonically cleaned, as no residual scent persists thereon. Further advantageously, the scent released by scent producing apparatus 900 does not persist in the vicinity of scent producing apparatus 900 for more than a pre-determined amount of time and a newly produced scent does not mix with previous scents.

FIG. 2 illustrates a high level schematic diagram of a driving circuitry 800, comprising: a pulse generator 810; a first driver 820; a second driver 830; and a control circuitry 250. In one embodiment, driving circuitry 800 is located on a printed circuit board. Optionally, a plurality of low liquid sensors each associated with a particular one of the plurality of scent reservoirs 20 of FIGS. 1A-1I are further provided in communication with control circuitry 250 and are arranged to output an alarm when the quantity of liquid in the respective scent reservoir 20 is less than a predetermined amount. Pulse generator 810 preferably comprises: a low frequency functionality 850; a high frequency functionality 860; and an ultrasonic cleaning functionality 870. Control circuitry 250 is in communication with each of pulse generator 810, first driver 820 and second driver 830. A first output of pulse generator 810 is connected, via first driver 820, to vibration mechanism 1040 of FIG. 1A and a second output of pulse generator 810 is connected to second driver 830. Each of a plurality of outputs of second driver 830 is connected to a respective one of the plurality of first and second translation mechanisms 1060 and 1070 of FIG. 1A.

In operation, and as described above, control circuitry 250 operates low frequency functionality 850 to generate a low frequency electrical signal, which is driven towards a plurality of first and second translation mechanisms 1060 and 1070 by second driver 830, thereby releasing a controlled quantity of super-concentrated volatile scent liquid and a controlled quantity of common solvent from at least one controllable release mechanism 930. As described above, in one embodiment, the released controlled quantity of common solvent is about 20 times greater than the released controlled quantity of super-concentrated volatile scent liquid.

For operation of atomizer 920, as described above in relation to FIGS. 1A-1I, control circuitry 250 further operates high frequency functionality 860 to generate a high frequency signal which is driven towards vibration mechanism 1040 by first driver 820, thereby vibration mechanism 1040 is vibrated, as described above.

In the embodiment where segmented nozzle device 960 is not provided, when production of a scent is ceased, as described above, control circuitry 250 operates ultrasonic cleaning functionality 870 to perform ultrasonic cleaning by providing vibrating energy to vibration mechanism 1040. In one non-limiting embodiment, ultrasonic cleaning functionality 870 is arranged to output an electric power of 40 kHz to 400 kHz. In one embodiment, ultrasonic cleaning functionality 870 is arranged to perform ultrasonic cleaning in the absence of both low frequency electrical signal from low frequency functionality 850 and high frequency electrical signal from high frequency functionality 860.

Figure 3A:
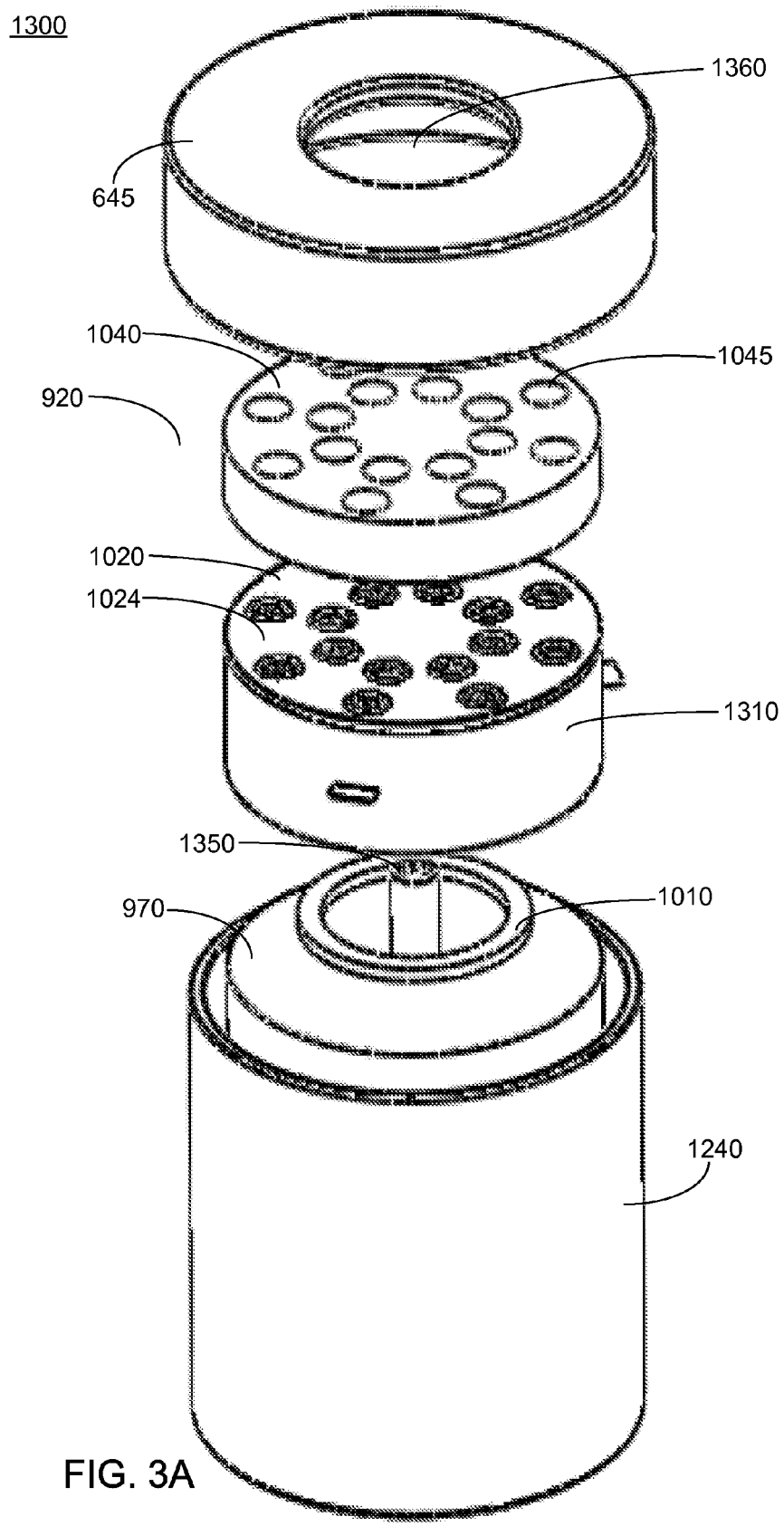
FIGS. 3A-3C illustrate a plurality of views of an exemplary embodiment of a scent producing apparatus comprising a single-scent cartridge in communication with an atomizer.
Figure 3B:
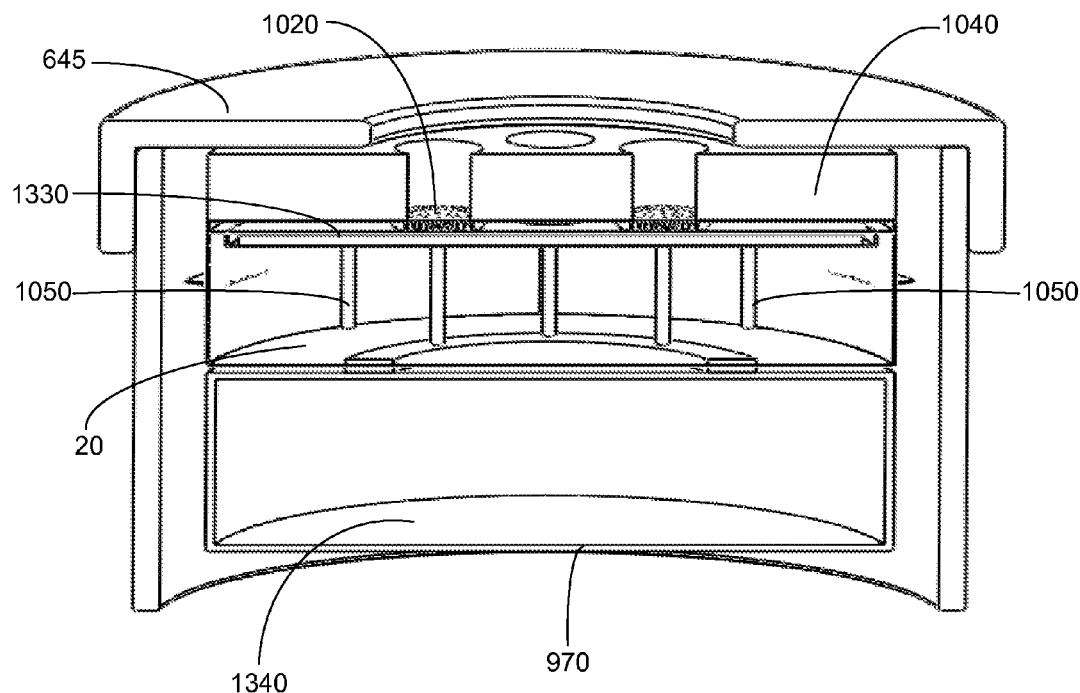
Figure 3C:
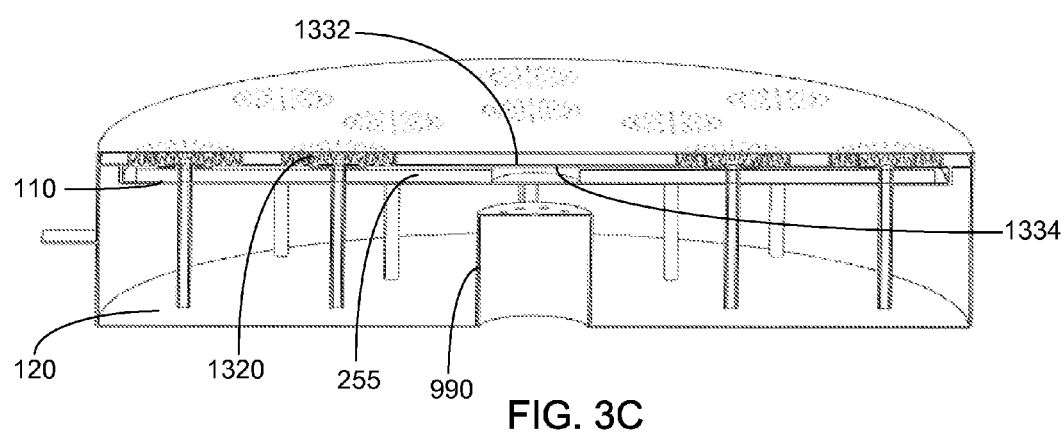

FIG. 3A illustrates a perspective view of various components of a scent producing apparatus 1300, comprising a scent cartridge 1310 in communication with an atomizer 920; FIG. 3B illustrates a side cut view of scent producing apparatus 1300 exhibiting a ring shaped vibration mechanism; and FIG. 3C illustrates a side cut view of scent cartridge 1310 in communication with atomizer 920 and exhibiting a plurality of controllable release mechanisms 1320, FIGS. 3A-3C being taken together.

In further detail, scent producing apparatus 1300 comprises: scent cartridge 1310; atomizer 920; plurality of controllable release mechanisms 1320; a common base 1330, exhibiting a first face 1332 and a second face 1334 opposing first face 1332; a housing 970, forming an external scent reservoir 1340 and comprising volatile scent liquid 1160 (not shown), as described above in relation to FIGS. 1A-1I; a housing extension 990, exhibiting a plurality of scent exit ports 1350; a vibration isolation ring 1010; a printed circuit board (PCB) 255 comprising a control circuitry 250 (not shown); and a sealing ring 645, exhibiting an aperture 1360. Atomizer 920 is as described above in relation to FIGS. 1A-1I. As described above, in one embodiment vibration mechanism 1040 is disc shaped. In another embodiment (not shown), vibration mechanism 1040 is ring shaped. Controllable release mechanisms 1320 are in all respects similar to controllable release mechanisms 930 of FIGS. 1A-1I, with the exception that local portions 1110 of solvent reservoir 980 and the respective second translation mechanisms 1070 are not provided. Common base 1330 has disposed on first face 1332 a plurality of controllable release mechanism 1320, as described above in relation to common base 940 of FIGS. 1A-1I. PCB 255 is in communication with each of first translation mechanisms 1060. External scent reservoir 1340 is particularly external of scent cartridge 1310.

Scent cartridge 1310 is in all respects similar to multi-scent cartridge 910 of FIGS. 1A-1I, with the exception that only one scent reservoir 20 is provided. Input port 1050 of each controllable release mechanism 1320 extends through common base 1330 into scent reservoir 20. Scent reservoir 20 comprises a first wall 110 and a second wall 120. In one embodiment, input ports 1050 operate by capillary action and in one further embodiment input ports 1050 extend longitudinally through first wall 110 to a location proximate to second wall 120 such that even a minimal amount of volatile scent liquid located in scent reservoir 20 is pulled through input ports 1050 by capillary action. Housing extension 990 extends into scent reservoir 20 and is arranged to pass volatile scent liquid from external scent reservoir 1340 into scent reservoir 20, via scent exit ports 1350. As described above, in one embodiment housing extension 990 comprises a one-way valve, allowing for volatile scent liquid to flow only into scent reservoir 20. Vibration isolation ring 1010 is arranged to isolate housing 970 from scent cartridge 1310 such that when scent cartridge 1310 is vibrated housing 970 is not vibrated. Atomizer 920 and controllable release mechanisms 1320 are in communication as described above in relation to atomizer 920 and plurality of controllable release mechanisms 930 of FIGS. 1A-1I. Sealing ring 645 is connected to vibration mechanism 1040, defining an end of scent producing apparatus 1300. In one embodiment, housing 970, scent cartridge 1310 and atomizer 920 are placed inside an outer housing 1240 and sealing ring 645 is placed external of outer housing 1240.

As described above, in one embodiment, housing 970 is removable and external scent reservoir 1340 can be refilled when exhausted of volatile scent liquid. In another embodiment, an opening (not shown) is provided in housing 970 to allow refilling of external scent reservoir 1340 when exhausted of volatile scent liquid. Volatile scent liquid stored in external scent reservoir 1340 is arranged to enter housing extension 990, aided by the force of gravity. Volatile scent liquid then enters scent reservoir 20.

The operation of controllable release mechanisms 1320 is in all respects similar to the operation of controllable release mechanisms 930 of FIGS. 1A-1I. As described above, a controlled quantity of volatile scent liquid is released onto second face 1024 of atomizer plate 1020.

In order to produce a scent, control circuitry 250 is arranged to provide a high frequency electrical signal to vibration mechanism 1040 thereby vibrating atomizer plate 1020 and atomizing any volatile scent liquid found thereon second face 1024 of atomizer plate 1020. In an exemplary embodiment the high frequency electrical signal exhibits a frequency range of 1-2 MHz, however this is not meant to be limiting in any way. The atomized volatile scent liquid is released through aperture 1360 to be scented distal of scent producing apparatus 1300. In order to cease the production of the scent, control circuitry 250 is arranged to disconnect the electrical signal from vibration mechanism 1040 and in response atomizer plate 1020 ceases to vibrate.

Figure 4:
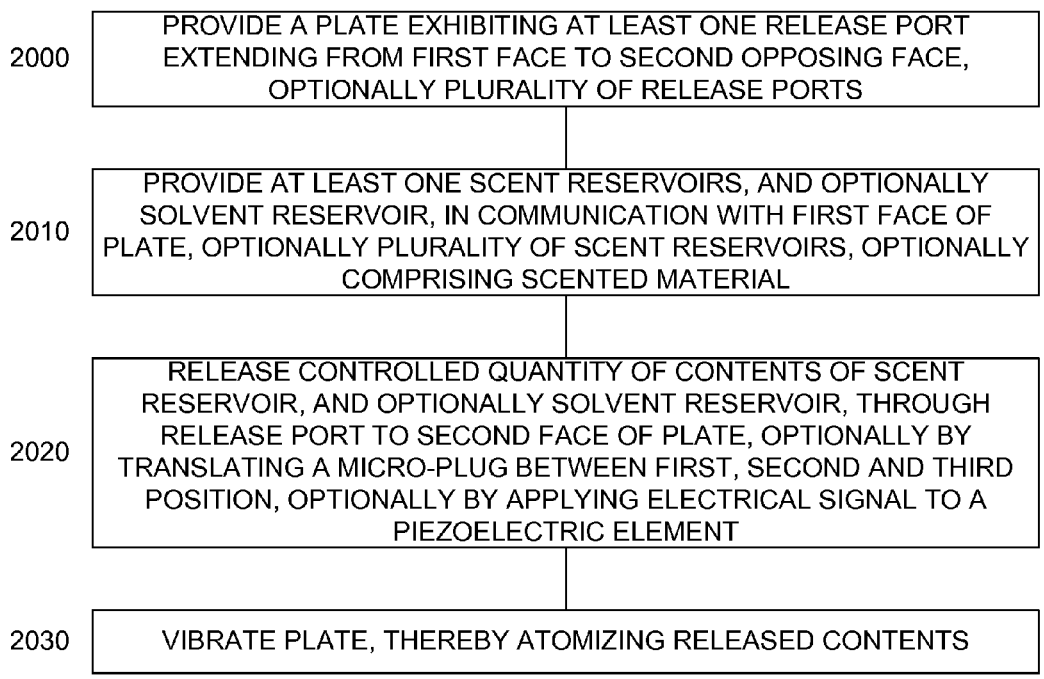
FIG. 4 illustrates a high level flow chart of the operation of the scent producing apparatus of FIGS. 1A-1I and the scent producing apparatus of FIGS. 2A-2C.

FIG. 4 illustrates a high level flow chart of a method of scent production. In stage 2000, a plate is provided exhibiting at least one release port extending from a first face of the provided plate to a second face of the provided plate, the second face opposing the first face. Optionally, the at least one release port comprises a plurality of release ports. In stage 2010, at least one scent reservoir is provided in communication with the first face of the plate. In one embodiment, each scent reservoir comprises a scented material. In one embodiment, a plurality of scent reservoirs are provided. Optionally, a solvent reservoir is further provided in communication with the first face of the plate.

In stage 2020, a controlled quantity of each provided scent reservoir of stage 2010 is released through a respective release port of the provided plate of stage 2000 to the second face of the plate. In one embodiment, a controlled quantity of the contents of the optionally provided solvent reservoir of stage 2010 is released through a respective release port of the provided plate. In one embodiment, the release of the contents of each provided scent reservoir and the optional release of the contents of the optionally provided solvent reservoir comprises translating a respective micro-needle between a first, second and third position, as described above in relation to FIGS. 1G-1I. In one embodiment, the translating of each respective micro-needle comprises applying an electrical signal to a piezoelectric element, as described above in relation to first and second translation mechanism 1060 and 1070. In stage 2030, the provided plate of stage 2000 is vibrated, thereby atomizing the released contents of the provided at least one scent reservoir and the released contents of the optionally provided solvent reservoir of stage 2010.

Figure 5:
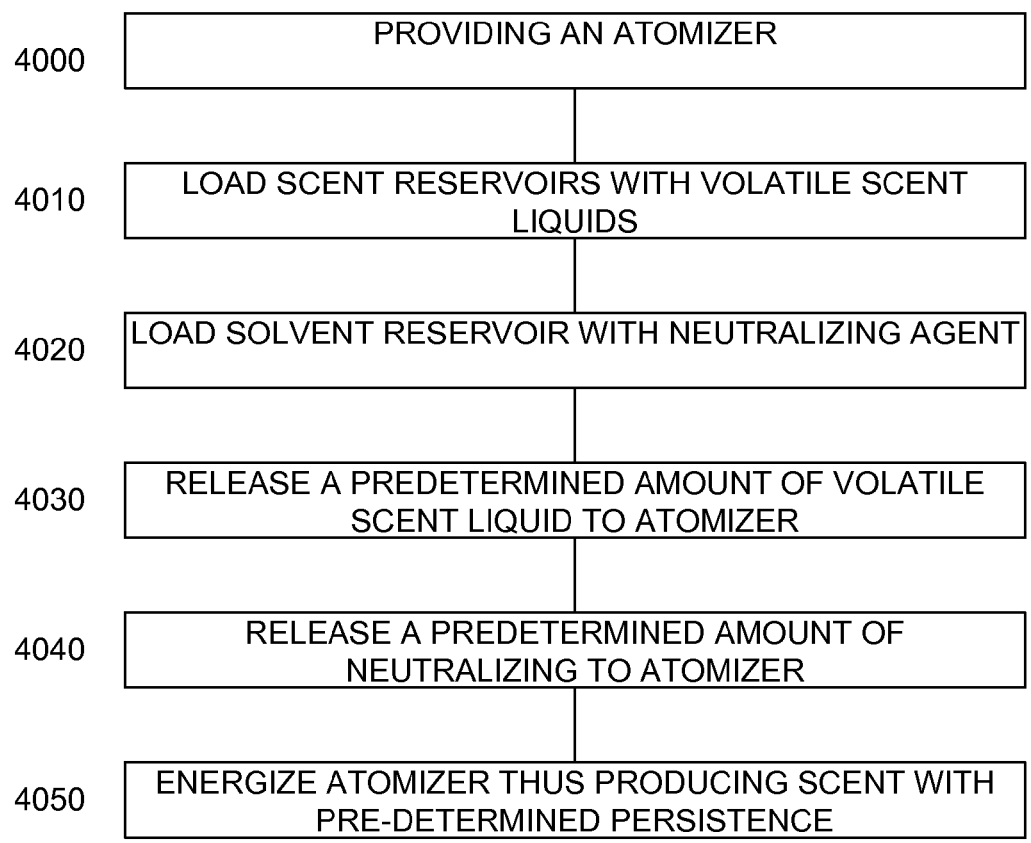
FIG. 5 illustrates a high level flow chart of an embodiment of a method of scent production utilizing a neutralizing agent to achieve a pre-determined persistence.

FIG. 5 illustrates a high level flow chart of an embodiment of a method of scent production utilizing a neutralizing agent to achieve a pre-determined persistence. The method of FIG. 5 may be advantageously utilized with scent producing apparatus 900, as described above. In stage 4000, an atomizer is provided, such as atomizer 920 described above.

In stage 4010, each of the various scent reservoirs 20 are loaded with a particular volatile scent liquid. There is no requirement that each and every scent reservoir 20 be loaded with a unique volatile scent liquid, and a plurality of scent reservoirs 20 may be loaded with an identical volatile scent liquid without exceeding the scope.

In stage 4020, solvent reservoir 980 is loaded with a neutralizing agent. In one embodiment the neutralizing agent is an amphoteric substance arranged to neutralize any scent produced by the respective scent producing apparatus after a pre-determined time period. In one particular embodiment the neutralizing agent is a sodium bicarbonate solution. In another embodiment the neutralizing agent is a strongly basic liquid, preferably exhibiting a pH of greater than 9 to neutralize any acidic volatile scent liquid.

In stage 4030, a pre-determined quantity of one or more volatile scent liquids are released to the atomizer as described above, and in stage 4040 a pre-determined quantity of the neutralizing agent is further released to the atomizer. In stage 4050, the atomizer is energized thus atomizing the mix of volatile scent liquid and neutralizing agent to produce a scent with pre-determined persistence. The neutralizing agent preferably acts a solvent for production of the scent, and equally acts to neutralize the scent after a pre-determined time period.

Figure 6A:
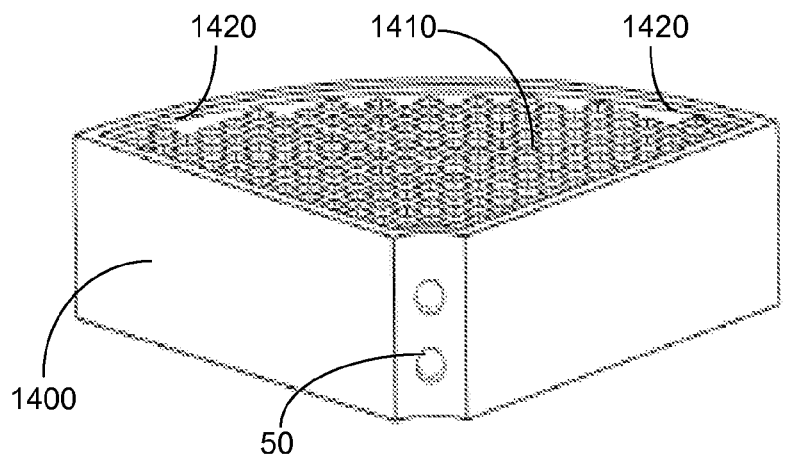
FIG. 6A illustrates a perspective view of a scent reservoir comprising scented material.

FIG. 6A illustrates a perspective view of a scent reservoir 1400. Scent reservoir 1400 is in all respects similar to scent reservoir 20 of FIGS. 1A-1I, with the exception that scent reservoir 1400 comprises an inner mesh 1410 and exhibits a plurality of holes 50. In one embodiment, inner mesh 1410 is impregnated with a scent. In another embodiment, inner mesh 1410 is coated with a scent. In one embodiment, inner mesh 1410 is composed of plastic. In one embodiment, the inner walls 1420 of scent reservoir 1400 are impregnated with a scent. In another embodiment, inner walls 1420 of scent reservoir 1400 are coated with a scent. In one embodiment, inner walls 1420 of scent reservoir 1400 are composed of plastic. Common solvent in scent reservoir 1400 absorbs scent from inner mesh 1410 and inner walls 1420.

Figure 6B:
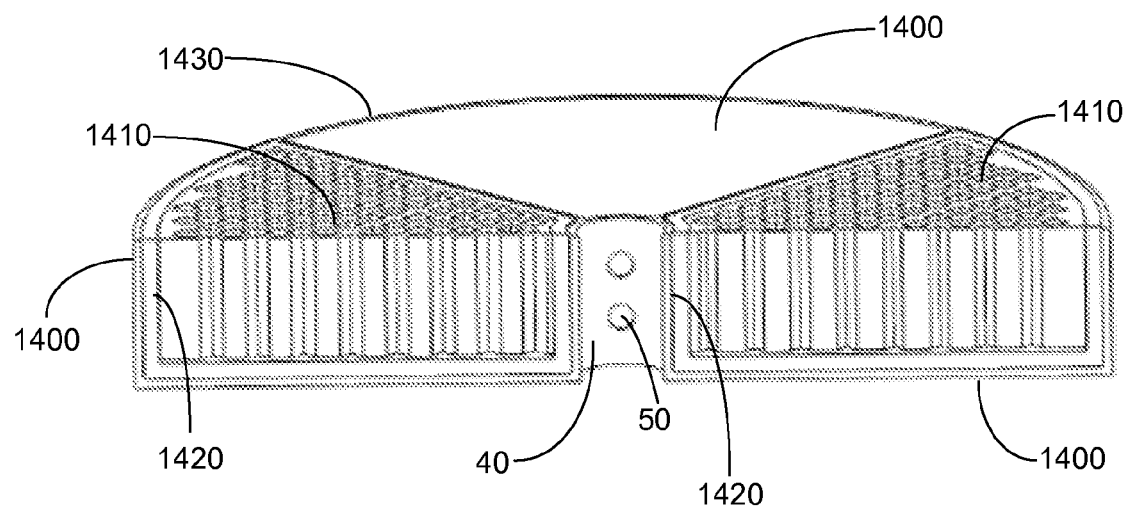
FIG. 6B illustrates a side cut view of a multi-scent cartridge comprising a plurality of the scent reservoirs of FIG. 6A.

FIG. 6B illustrates a side cut view of a multi-scent cartridge 1430. Multi-scent cartridge 1430 is in all respects similar to multi-scent cartridge 910 of FIGS. 1A-1I, with the exception that scent reservoirs 20 are replaced with scent reservoirs 1400 of FIG. 6A.

In one embodiment, multi-scent cartridge 1430 replaces multi-scent cartridge 910 in scent producing apparatus 900 of FIGS. 1A-1I. In one embodiment, scent cartridge 1310 of FIGS. 3A-3C is replaced with a scent cartridge comprising scented material, as described in relation to scent reservoir 1400.

Figure 6C:
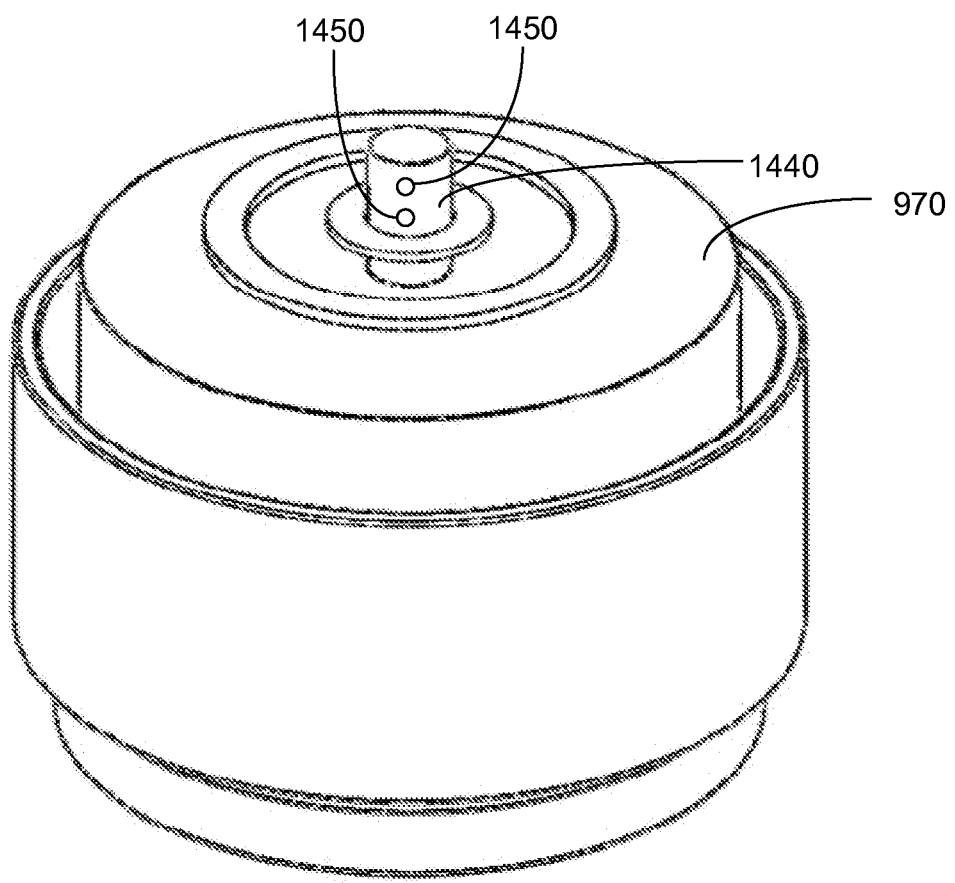
FIG. 6C illustrates a perspective view of a solvent reservoir arranged to be used in cooperation with the multi-scent cartridge of FIG. 6B.

FIG. 6C illustrates a perspective view of housing 970 and a housing extension 1440. Housing extension 1440 is in all respects similar to housing extension 990 of FIG. 1A with the exception that holes 1000 at a base of housing extension 990 are replaced with a plurality of holes 1450 along the length of housing extension 1440. Holes 1450 of housing extension 1440 are positioned in relation to holes 50 of scent reservoirs 1400 such that solvent exiting holes 1450 enters scent reservoirs 1400 via respective holes 50. Advantageously, temporary solvent reservoir 1130 and local portions 1110 of solvent reservoir 980 are not required.

Figure 7A:
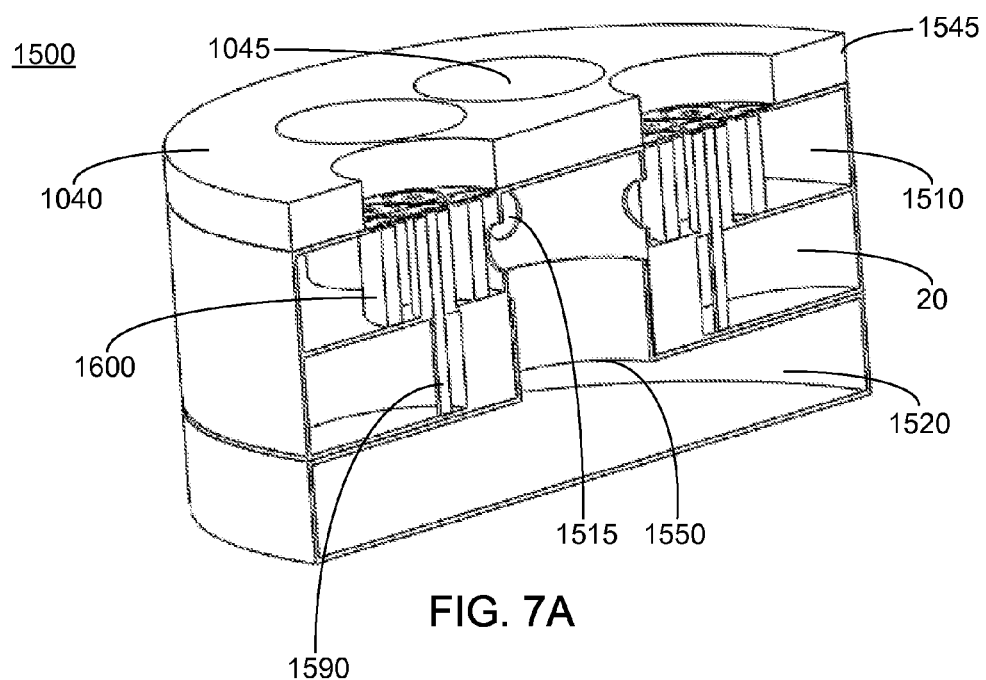
FIGS. 7A-7G illustrate a plurality of views of various components of a scent producing apparatus comprising a plurality of solvent release mechanisms for each scent release mechanism.
Figure 7B:
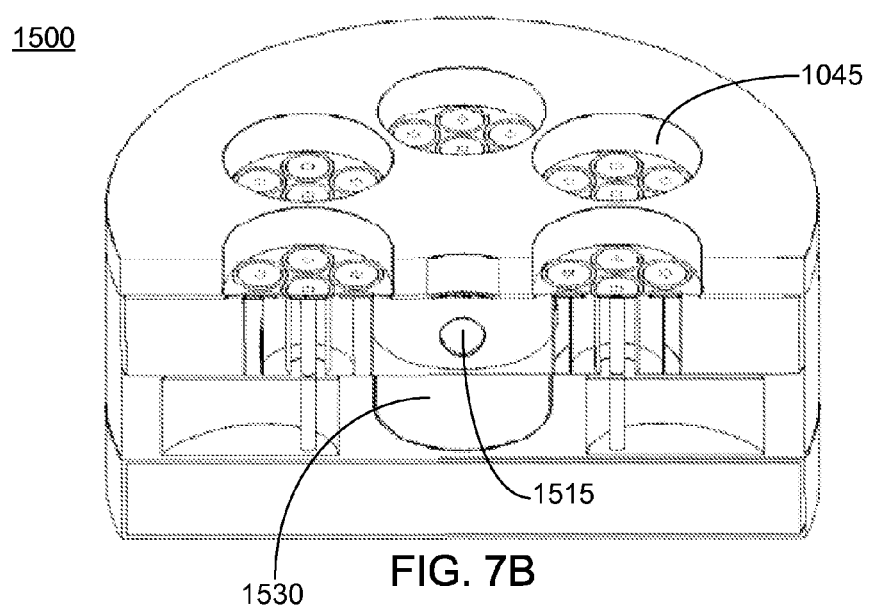
Figure 7C:
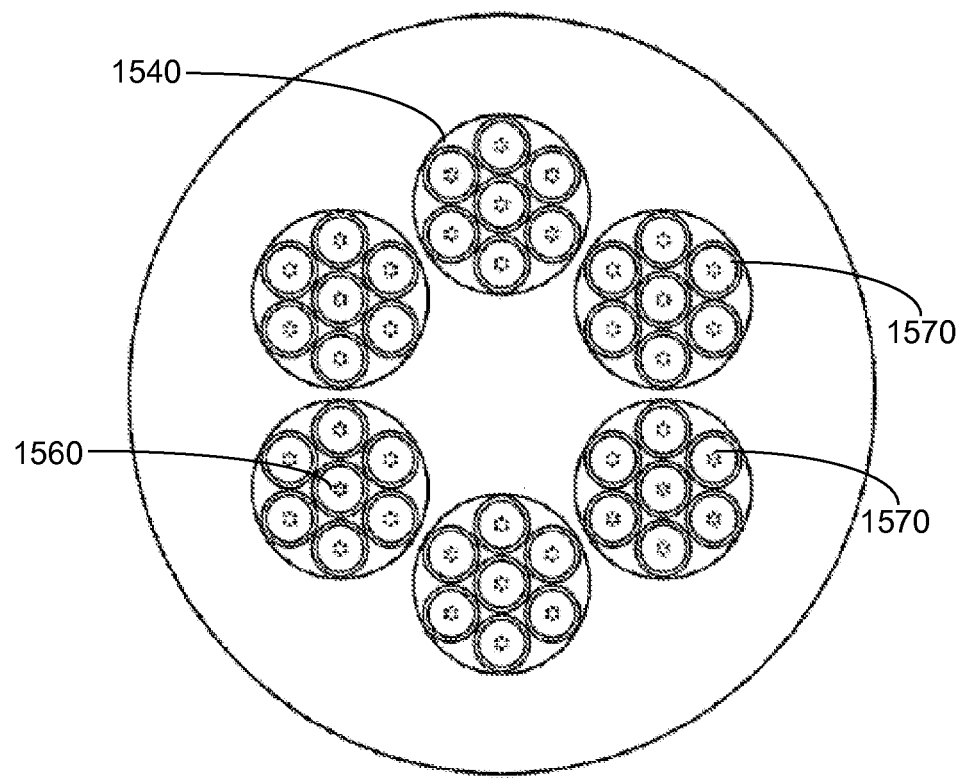
Figure 7D:
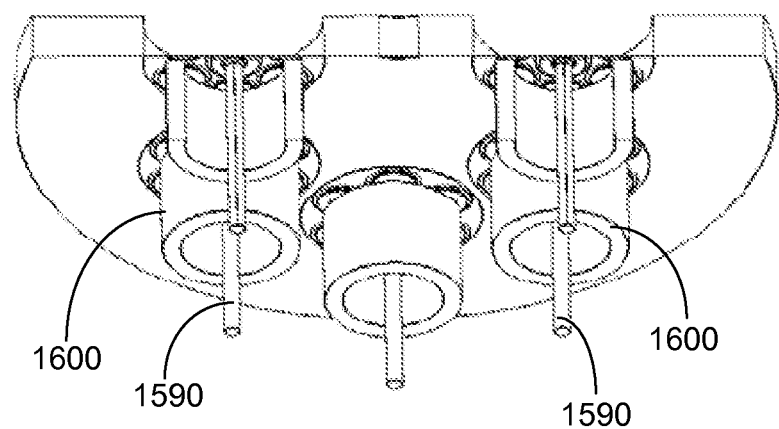
Figure 7E:
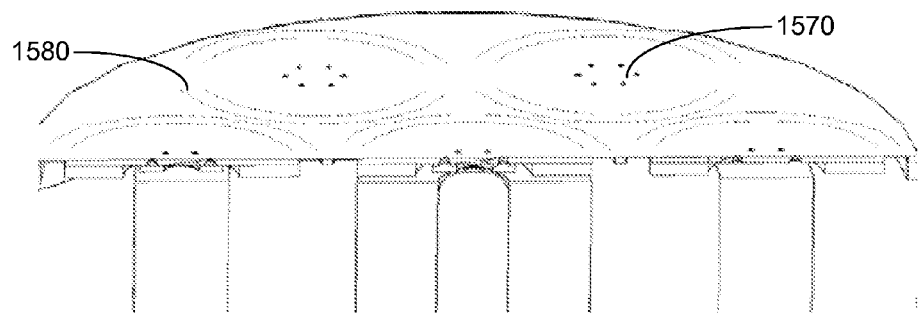
Figure 7F:
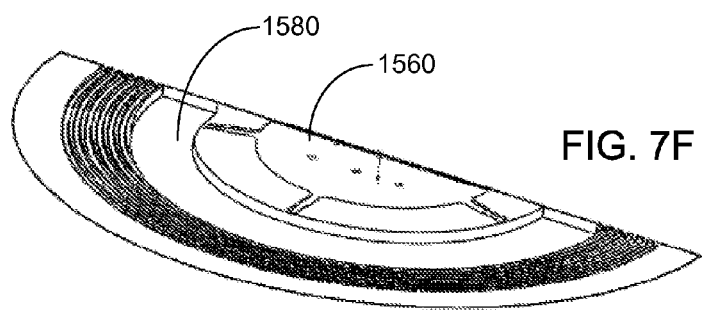
Figure 7G:
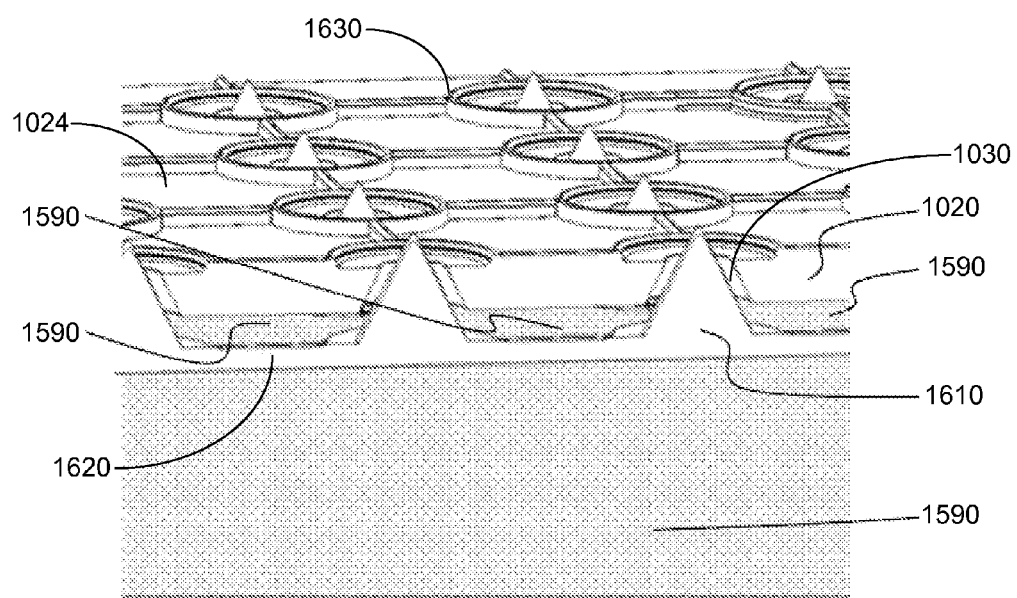

FIG. 7A illustrates a first side cut view of a scent producing apparatus 1500; FIG. 7B illustrates a second side cut view of scent producing apparatus 1500; FIG. 7C illustrates a top view of scent producing apparatus 1500; FIG. 7D illustrates a side cut view of various components of scent producing apparatus 1500; FIG. 7E illustrates a side cut view of a top half of scent producing apparatus 1500; FIG. 7F illustrates a cut away perspective view of a top portion of a controllable release mechanism of scent producing apparatus 1500; and FIG. 7G illustrates a perspective view of a portion of a micro-valve array of scent producing apparatus 1500, FIGS. 7A-7G being described together.

Scent producing apparatus 1500 comprises: a plurality of scent reservoirs 20; a solvent reservoir 1510, exhibiting a plurality of ports 1515; a main solvent reservoir 1520; a solvent reservoir extension 1530; a plurality of controllable release mechanisms 1540; and an atomizer 1545.

Solvent reservoir 1510 is in one embodiment ring shaped surrounding an upper portion of solvent reservoir extension 1530. Plurality of scent reservoirs 20 are in one embodiment radially arranged around a lower portion of solvent reservoir extension. Main solvent reservoir 1520 is juxtaposed with the plurality of scent reservoirs 20 and exhibits an opening 1550, opening 1550 connecting main solvent reservoir 1520 to solvent reservoir extension 1530, main solvent reservoir 1520 being in all respects similar to solvent reservoir 980 of FIGS. 1A-1I. Solvent reservoir 1510 is in communication with solvent reservoir extension 1530 via ports 1515.

Each controllable release mechanism 1540 comprises: a scent release mechanism 1560, associated with a particular scent reservoir 20; a plurality of solvent release mechanisms 1570; a plurality of translation mechanisms 1580; a scent capillary wick 1590; and a solvent capillary wick 1600. Scent release mechanism 1560 and solvent release mechanisms 1570 each comprise a plurality of micro-needles 1610, which are in all respects similar to optional micro-needles 125 of FIGS. 1A-1I, each micro-needle 1610 forming the needle section of a particular micro valve. Micro-needles 1610 of each scent release mechanism 1560 and solvent release mechanism 1570 are arranged in a plurality of arrays 1620, each array 1620 comprising a plurality of micro-needles 1610 connected in series, preferably connected in a curvilinear fashion such that each array 1620 is circular. A first end of scent capillary wick 1590 is disposed in between adjacent arrays 1620 of scent release mechanism 1560 and extends through solvent reservoir 1510 to a second end which is situated within the associated scent reservoir 20. Solvent capillary wick 1600 is arranged to commonly connect solvent release mechanisms 1570 to solvent reservoir 1510. Specifically, a first end of solvent capillary wick 1600 is disposed in between adjacent arrays 1620 of solvent release mechanisms 1570 and a second end of solvent capillary wick 1600 is situated within solvent reservoir 1510. In one embodiment, the plurality of solvent release mechanisms 1570 are radially arranged about scent release mechanism 1560. Scent release mechanism 1560 and solvent release mechanisms 1570 are each in communication with a particular translation mechanism 1580. In one embodiment, each translation mechanism 1580 is ring shaped and is arranged to surround the respective scent release mechanism 1560 or solvent release mechanism 1570. In one embodiment, each translation mechanism 1580 comprises a piezoelectric element, as described above in relation first and second translation mechanisms 1160, 1170 of FIGS. 1A-1I.

Atomizer 1545 is in all respects similar to atomizer 920 of FIGS. 1A-1I, with the exception that each release port 1030 exhibits a border 1630 extending longitudinally from second face 1024 of plate 1020. As described above in relation to FIGS. 1A-1I, each micro-needle 1610 is arranged to mate with a respective one of release ports 1030, thereby forming a micro-valve, each release port 1030 forming the chassis section of a particular micro-valve. As described above, in one embodiment vibration mechanism 1040 is disc shaped and exhibits a plurality of holes 1045 extending therethrough.

Each hole 1045 is arranged to be aligned with the plurality of micro-valves associated with a particular controllable release mechanism 1540.

In operation, volatile scent liquid stored in scent reservoirs 20 is transferred to each scent release mechanism 1560 via the respective scent capillary wick 1590 and common solvent stored in solvent reservoir 1510 is transferred to each solvent release mechanism 1570 via the respective solvent capillary wick 1600. The operation of controllable release mechanisms 1540 is in all respects similar to the operation of controllable release mechanisms 930 of FIGS. 1A-1I. As described above, translation mechanism 1580 translates each of the respective micro-needles 1610 between a first position wherein micro-needle 1610 is seated within the respective release port 1030, preferably seated flush, a second position wherein micro-needle 1610 is at least partially removed from a wall of the respective release port 1030, and a third position being between the first position and the second position, a drop of volatile scent liquid or common solvent being released through the respective release port when micro-needle 1610 is translated to the third position from the second position. Any released droplets are contained within the respective border 1630.

In order to produce a scent, translation mechanisms 1580 of a particular controllable release mechanism 1540 are arranged to release a droplet of volatile scent liquid via the respective scent release mechanism 1590 and droplets of common solvent via the respective solvent release mechanisms 1600, as described above. The droplets are then atomized by atomizer 1545, as described above in relation to atomizer 920 of FIGS. 1A-1I. In order to produce a compound scent, translation mechanisms 1580 of a plurality of controllable release mechanisms 1540 are arranged to release droplets of volatile scent liquid via the respective scent release mechanisms 1590 and droplets of common solvent via the respective solvent release mechanisms 1600, as described above. The droplets are then atomized by atomizer 1545, as described above.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

We claim:

1. A scent producing apparatus, the apparatus comprising:
a control circuitry;
a plate exhibiting at least one release port extending from a first face of said plate to a second face of said plate opposing said first face;
at least two scent reservoirs in communication with said first face of said plate;
a controllable scent release mechanism associated with each scent reservoir and arranged to release a controlled quantity of the contents of the associated scent reservoir through said at least one release port to said second face of said plate; and
a vibrator responsive to said control circuitry and in communication with said plate,
wherein said control circuitry is arranged to:
control each controllable scent release mechanism to release a controlled quantity of the contents of the associated scent reservoir through said at least one release port to said second face of said plate;
and vibrate said plate to thereby atomize the released contents of said at least one scent reservoir,
wherein each controllable scent release mechanism further comprises:
a scent release micro-needle, in communication with said first face of said plate, extending longitudinally from a base end to a tip end, and arranged to mate with a respective release port; and
a scent release translation mechanism in communication with said scent release micro-needle and responsive to said control circuitry,
wherein said control circuitry is further arranged to translate, via said scent release translation mechanism, said scent release micro-needle in relation to said plate from a first position, wherein said scent release micro-needle is seated within the respective release port, to a second position wherein said scent release micro-needle is at least partially removed from a wall of said respective release port, and
wherein said control of each controllable release mechanism to release a controlled quantity of the contents of the associated scent reservoir is responsive to the respective scent release micro-needle being in said second position.

2. The scent producing apparatus of claim 1, wherein each controllable scent release mechanism comprises a local portion of said at least one scent reservoir.

3. The scent producing apparatus of claim 1, wherein said scent release translation mechanism comprises a scent release piezoelectric element.

4. The scent producing apparatus of claim 1, wherein said controllable scent release mechanism comprises a scent release piezoelectric element.

5. The scent producing apparatus of claim 1, wherein said at least one scent reservoir comprises a plurality of scent reservoirs and said at least one release port comprises a plurality of release ports each associated with a particular controllable scent release mechanisms,
said arrangement of said control circuitry to control each controllable scent release mechanism to release a controlled quantity of the contents of the associated scent reservoir comprises an arrangement to control each controllable scent release mechanism to release a controlled quantity of the contents of the associated scent reservoir through the associated release port to said second face of said plate.

6. The scent producing apparatus according to claim 1, further comprising:
- a solvent reservoir in communication with said first face of said plate; and
- at least one controllable solvent release mechanism associated with said solvent reservoir and arranged to release a controlled quantity of the contents of said solvent reservoir through said at least one release port to said second face of said plate,
- wherein said control circuitry is further arranged to control said at least one controllable solvent release mechanism to release a controlled quantity of the contents of said solvent reservoir through said at least one release port to said second face of said plate.

7. The scent producing apparatus according to claim 6, wherein each controllable solvent release mechanism further comprises a local portion of said solvent reservoir.

8. The scent producing apparatus according to claim 6, wherein each controllable solvent release mechanism further comprises:
- a solvent release micro-needle, in communication with said first face of said plate, extending longitudinally from a base end to a tip end, and arranged to mate with a respective release port; and
- a solvent release translation mechanism in communication with said solvent release micro-needle and responsive to said control circuitry,
- wherein said control circuitry is further arranged to translate, via said solvent release translation mechanism, said solvent release micro-needle in relation to said plate from a first position,
- wherein said solvent release micro-needle is seated within the respective release port, to a second position wherein said solvent release micro-needle is at least partially removed from a wall of the respective release port, and
- wherein said control of each controllable release mechanism to release a controlled quantity of the contents of said solvent reservoir is responsive to the respective solvent release micro-needle being in said second position.

9. The scent producing apparatus according to claim 8, wherein said solvent release translation mechanism comprises a solvent release piezoelectric element.

10. The scent producing apparatus according to claim 6, wherein said controllable solvent release mechanism comprises a solvent release piezoelectric element.

11. The scent producing apparatus according to claim 6, wherein said at least one controllable scent release mechanism comprises a plurality of controllable scent release mechanisms, and
- wherein said at least one controllable solvent release mechanism comprises a plurality of controllable solvent release mechanisms, each associated with a particular one of said plurality of controllable scent release mechanisms.

12. The scent producing apparatus according to claim 1, wherein each scent reservoir comprises a scented material.

13. A method of producing a scent, the method comprising:
- providing a plate exhibiting at least one release port extending from a first face of said provided plate to a second face of said provided plate opposing said first face;
- providing at least two scent reservoirs in communication with said first face of said provided plate;
- releasing a controlled quantity of the contents of said provided at least one scent reservoir through said at least one release port to said second face of said provided plate; and
- vibrating said provided plate to thereby atomize the released contents of said provided at least one scent reservoir,
- wherein each provided controllable scent release mechanism further comprises:
- a scent release micro-needle, in communication with said first face of said provided plate, extending longitudinally from a base end to a tip end, and arranged to mate with a respective release port,
- wherein the method further comprises translating said scent release micro-needle in relation to said provided plate from a first position, wherein said scent release micro-needle is seated within the respective release port, to a second position wherein said scent release micro-needle is at least partially removed from a wall of the respective release port, and
- wherein said releasing a controlled quantity of the contents of said provided at least one scent reservoir is responsive to the respective scent release micro-needle being in said second position.

14. The method according to claim 13, further comprising:
- providing a controllable scent release mechanism associated with each provided scent reservoir, said releasing a controlled quantity of the contents of each provided scent reservoir being responsive to the provided associated controllable scent release mechanism,
- wherein each provided controllable scent release mechanism comprises a local portion of the provided associated scent reservoir.

15. The method according to claim 14, further comprising:
- providing a scent release piezoelectric element in communication with said local portion of each provided scent reservoir,
- wherein said translating each scent release micro-needle comprises applying an electrical signal to the associated provided scent release piezoelectric element.

16. The method according to claim 13, further comprising:
- providing a scent release piezoelectric element in communication with each provided scent reservoir,
- wherein said releasing a controlled quantity of the contents of each provided scent reservoir comprises applying an electrical signal to the associated provided scent release piezoelectric element.

17. The method according to claim 13, wherein said provided at least one scent reservoir comprises a plurality of scent reservoirs and said at least one release port comprises a plurality of release ports each associated with a particular scent reservoir,
- said releasing a controlled quantity of the contents of each provided scent reservoir comprises releasing a controlled quantity of the contents of the particular provided scent reservoir through the associated release port to said second face of said provided plate.

18. The method according to claim 13, further comprising:
- providing a solvent reservoir in communication with said first face of said plate; and
- releasing a controlled quantity of the contents of said provided solvent reservoir through said at least one release port to said second face of said provided plate.

19. The method according to claim 18, further comprising:
- providing at least one controllable solvent release mechanism associated with said provided solvent reservoir, said releasing a controlled quantity of the contents of said provided solvent reservoir being responsive to said provided at least one controllable solvent release mechanism,
wherein each controllable solvent release mechanism further comprises a local portion of said provided solvent reservoir.

20. The method according to claim 19, wherein each provided controllable solvent release mechanism further comprises:
a solvent release micro-needle, in communication with said first face of said provided plate, extending longitudinally from a base end to a tip end, and arranged to mate with said at least one release port,
wherein the method further comprises translating said solvent release micro-needle in relation to said provided plate from a first position, wherein said solvent release micro-needle is seated within the respective release port, to a second position wherein said solvent release micro-needle is at least partially removed from a wall of the respective release port, and
wherein said releasing a controlled quantity of the contents of said provided solvent reservoir is responsive to at least one scent release micro-needle being in said second position.

21. The method according to claim 20, further comprising:
providing a solvent release piezoelectric element in communication with each local portion of said provided solvent reservoir,
wherein said translating each solvent release micro-needle comprises applying an electrical signal to the associated provided solvent release piezoelectric element.

22. The method according to claim 19, further comprising:
providing a solvent release piezoelectric element in communication with each local portion of said provided solvent reservoir,
wherein said releasing a controlled quantity of the contents of said provided solvent reservoir comprises applying an electrical signal to a provided solvent release piezoelectric element.

23. The method according to claim 19, wherein said at least one controllable scent release mechanism comprises a plurality of controllable scent release mechanisms, and
wherein said at least one controllable solvent release mechanism comprises a plurality of controllable solvent release mechanisms, each associated with a particular one of said plurality of controllable scent release mechanisms.

24. The method according to claim 13, wherein each provided scent reservoir comprises a scented material.

25. The method according to claim 13, further comprising:
releasing a pre-determined quantity of neutralizing agent through said at least one release port onto said second face of said provided plate, said released neutralizing agent arranged to neutralize a scent produced by said atomized contents of said at least one scent reservoir,
wherein said vibrating atomizes said released contents of said provided at least one scent reservoir and said released neutralizing agent.

\* \* \* \* \*